US012662688B2

(12) United States Patent
Buller et al.

(10) Patent No.: US 12,662,688 B2
(45) Date of Patent: Jun. 23, 2026

(54) SITE-SELECTIVE DEUTERATION OF AMINO ACIDS THROUGH DUAL PROTEIN CATALYSIS

(71) Applicant: Wisconsin Alumni Research Foundation, Madison, WI (US)

(72) Inventors: Andrew Buller, Madison, WI (US); Tyler Doyon, Eau Claire, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 505 days.

(21) Appl. No.: 18/179,946

(22) Filed: Mar. 7, 2023

(65) Prior Publication Data

US 2023/0279450 A1 Sep. 7, 2023

Related U.S. Application Data

(60) Provisional application No. 63/317,315, filed on Mar. 7, 2022.

(51) Int. Cl.

*C12P 13/00* (2006.01)
*C07C 227/16* (2006.01)
*C12N 9/88* (2006.01)

(52) U.S. Cl.

CPC .......... *C12P 13/005* (2013.01); *C07C 227/16* (2013.01); *C12N 9/88* (2013.01); *C12Y 404/01* (2013.01); *C07B 2200/05* (2013.01)

(58) Field of Classification Search

None

See application file for complete search history.

(56) References Cited

PUBLICATIONS

Whelan et al., Enzymatic transamination, the synthesis of alpha,beta, beta-trideutero-L-glutamic acid and alpha-deutero-L-glutamic acid, Aust. J. Chem 22, 1969, 1779-82. (Year: 1969).*

Cooper, Proton Magnetic Resonance Studies of Glutamate-Alanine Transaminase-catalyzed Deuterium Exchange, JBC 251, 1976, 1088-96. (Year: 1976).*

BRENDA:EC2.6.1.2, www.brenda-enzymes.org/enzyme.php?ecno=2.6.1.2, retrieved Jun. 13, 2025. (Year: 2025).*

Li et al., Deciphering the Biosynthetic Origin of L-allo-Isoleucine, JACS 138, 2016, 408-15. (Year: 2016).*

Chun et al., Biocatalytic, Stereoselective Deuteration of α-Amino Acids and Methyl Esters, ACS Catalysis, Oct. 2020: 7413-18. (Year: 2020).*

Doyon et al., Site-Selective Deuteration of Amino Acids through Dual-Protein Catalysis, JACS 144, Apr. 2022, 7327-36. (Year: 2022).*

Franco et al., Chemical Mechanism of the Branched-Chain Aminotransferase IlvE from *Mycobacterium tuberculosis*, Biochemistry 55, 2016, 6295-6303. (Year: 2016).*

Chanatry et al., Synthesis of α,β-Deuterated 15N Amino Acids Using a Coupled Glutamate Dehydrogenase-Branched-Chain Amino Acid Aminotransferase System, Analytical Biochem. 213, 1993, 147-151. (Year: 1993).*

Kuramitsu et al., Branched-Chain Amino Acid Aminotransferase of *Escherichia coli*: Nucleotide Sequence of the ilvE Gene and the Deduced Amino Acid Sequence, J. Biochem. 97, 1985, 993-999. (Year: 1985).*

"Room temperature," American Heritage Dictionary of the English Language, Fifth Ed., 2022, accessed Dec. 22, 2025, ahdictionary.com/word/search.html?q=room+temperature. (Year: 2022).*

Altschul et al., "Gapped BLAST and PSI-BLAST: a new generation of protein database search programs," *Nucleic Acids Res*. 25:3389-3402, 1997.

Atzrodt, J.; Derdau, V.; Kerr, W. J.; Reid, M. Deuterium- and Tritium-Labelled Compounds: Applications in the Life Sciences. *Angew. Chemie—Int. Ed*. 2018, 57(7), 1758-1784.

Bezsudnova, E. Y.; Boyko, K. M.; Popov, V. O. Properties of Bacterial and Archaeal Branched-Chain Amino Acid Aminotransferases. *Biochem*. 2017, 82 (13), 1572-1591.

Bhushan, R.; Brückner, H. Marfey's Reagent for Chiral Amino Acid Analysis: A Review. *Amino Acids* 2004, 27 (3-4), 231-247.

Buller, A. R.; Brinkmann-Chen, S.; Romney, D. K.; Herger, M.; Murciano-Calles, J.; Arnold, F. H. Directed Evolution of the Tryptophan Synthase β-Subunit for Stand-Alone Function Recapitulates Allosteric Activation. *Proc. Natl. Acad. Sci*. 2015, 112 (47), 14599-14604.

Busch, F.; Rajendran, C.; Heyn, K.; Schlee, S.; Merkl, R.; Sterner, R. Ancestral Tryptophan Synthase Reveals Functional Sophistication of Primordial Enzyme Complexes. *Cell Chem. Biol*. 2016, 23 (6), 709-715.

Chanatry, J. A.; Schafer, P. H.; Kim, M. S.; LeMaster, D. M. Synthesis of α,β-Deuterated 15N Amino Acids Using a Coupled Glutamate Dehydrogenase-Branched-Chain Amino Acid Aminotransferase System. *Anal. Biochem*. 1993, 213, 147-151.

Chen et al., Crystal structures of complexes of the branched-chain aminotransferase from Deinococcus radiodurans with α-ketoisocaproate and L-glutamate suggest the radiation resistance of this enzyme for catalysis, *J. Bacteriol*. 2012, 194: 6206.

Chun, S. W.; Narayan, A. R. H. Biocatalytic, Stereoselective Deuteration of α-Amino Acids and Methyl Esters. *ACS Catal*. 2020, 10 (13), 7413-7418.

Devereux et al., A comprehensive set of sequence analysis programs for the VAX, *Nucl. Acid Res*., 12:387-395, 1984.

(Continued)

*Primary Examiner* — Todd M Epstein

(74) *Attorney, Agent, or Firm* — Joseph T. Leone; Yanjun Ma; DeWitt LLP

(57) ABSTRACT

A method for site-selective deuteration of amino acids using a protein system having an aminotransferase (e.g., DsaD) and/or a small partner protein (e.g., DsaE). A non-deuterated amino acid is contacted with deuterium and an aminotransferase or a combination of an aminotransferase and a partner protein, to yield a Cα-deuterated or a Cα- and Cβ-deuterated amino acid. Cβ-deuterated amino acids can be accessed by contacting a Cα- and Cβ-deuterated amino acid with non-deuterium hydrogen and an aminotransferase to wash out the deuterium at the Cα carbon atom by the non-deuterium hydrogen.

13 Claims, 15 Drawing Sheets
(14 of 15 Drawing Sheet(s) Filed in Color)

Specification includes a Sequence Listing.

(56) References Cited

PUBLICATIONS

Easton, C. J.; Hutton, C. A. Synthesis of Each Stereoisomer of [3-$^2H_1$] Phenylalanine and Evaluation of the Stereochemical Course of the Reaction of (R)-Phenylalanine with (S)-Phenylalanine Ammonia-Lyase. *J. Chem. Soc. Perkin Trans.* Jan. 1994, 3545-3548.
Esaki, N.; Sawada, S.; Tanaka, H.; Soda, K. Enzymatic Preparation of Alpha- and Beta-Deuterated or Tritiated Amino Acids with L-Methionine Gamma-Lyase. *Anal. Biochem.* 1982, 119, 281-285.
Furuta, T.; Takahashi, H .; Kasuya, Y. Evidence for a Carbanion Intermediate in the Elimination of Ammonia from L-Histidine Catalyzed by Histidine Ammonia-Lyase. *J. Am. Chem. Soc.* 1990, 112, 3633-3636.
Gant, T. G. Using Deuterium in Drug Discovery: Leaving the Label in the Drug. *J. Med. Chem.* 2014, 57 (9), 3595-3611.
Golichowski, A.; Harruff, R. C.; Jenkins, W. T. The Effects of pH on the Rates of Isotope Exchange Catalyzed by Alanine Aminotransferase. *Arch. Biochem. Biophys.* 1977, 178, 459-467.
Grocholska, P.; Bachor, R. Trends in the Hydrogen-Deuterium Exchange at the Carbon Centers. Preparation of Internal Standards for Quantitative Analysis by LC-MS. *Molecules* 2021, 26, 2989-3014.
Guggenheim, S.; Flavin, M. Cystathionine Gamma-Synthase. A Pyridoxal Phosphate Enzyme Catalyzing Rapid Exchanges of Beta and Alpha Hydrogen Atoms in Amino Acids. *J. Biol. Chem.* 1969, 244 (22), 6217-6227.
Hadener, A.; Tamm, C. H. Synthesis of Specifically Labelled L-Phenylalanines Using Phenylalanine Ammonia Lyase Activity. *J. Label. Compd. Radiopharm.* 1987, 24 (11), 1291-1306.
Hanashima, S.; Ibata, Y.; Watanabe, H.; Yasuda, T.; Tsuchikawa, H.; Murata, M. Side-Chain Deuterated Cholesterol as a Molecular Probe to Determine Membrane Order and Cholesterol Partitioning. *Org. Biomol. Chem.* 2019, 17 (37), 8601-8610.
Hanson, K. R.; Wightman, R. H.; Staunton, J.; Battersby, A. R. Stereochemical Course of the Elimination Catalysed by L-Phenylalanine Ammonia-Lyase and the Configuration of 2-Benzamidocinnamic Azlactone. *J. Chem. Soc. D Chem. Commun.* 1971, No. 4, 185-186.
Homer, R. J.; Kim, M. S.; LeMaster, D. M. The Use of Cystathionine Gamma-Synthase in the Production of Alpha and Chiral Beta Deuterated Amino Acids. *Analytical Biochemistry*. 1993, pp. 211-215.
Hutson, S. Structure and Function of Branched Chain Aminotransferases. *Prog. Nucleic Acid Res. Mol. Biol.* 2001, 70, 175-206.
Jotun-Hein, Muscle et al., "MUSCLE: a multiple sequence alignment method with reduced time and space complexity," *BMC Bioinformatics* 5: 113, 2004.
Kelly, N. M.; Sutherland, A.; Willis, C. L. Syntheses of Amino Acids Incorporating Stable Isotopes. *Nat. Prod. Rep.* 1997, 14 (3), 205-220.
Kirby, G. W.; Michael, J. Labelling of Aromatic Amino-Acids Stereoselectively with Tritium in the β-Methylene Group: The Stereochemistry of Hydroxylation in the Biosynthesis of Haemanthamine. *J. Chem. Soc. D Chem. Commun.* 1971, No. 4, 187-188.
Krumbiegel, P. Large Deuterium Isotope Effects and Their Use: A Historical Review. *Isotopes Environ. Health Stud.* 2011, 47 (1), 1-17.
Larkin M. A., et al., CLUSTALW2, "ClustalW and ClustalX version 2," *Bioinformatics* 23(21): 2947-2948, 2007.
Lemaster, D. M. Deuterium Labelling in NMR Structural Analysis of Larger Proteins. *Q. Rev. Biophys.* 1990, 23, 133-174.
Li, Q.; Qin, X.; Liu, J.; Gui, C.; Wang, B.; Li, J.; Ju, J. Deciphering the Biosynthetic Origin of 1-allo-Isoleucine. *J. Am. Chem. Soc.* 2016, 138 (1), 408-415.
Long, G. J .; Whelan, B. D. J. Enzymatic Transamination: The Synthesis of α,β,β- Trideutero-L-Glutamic Acid and α-Deutero-L-Glutamic Acid. *Aust. J. Chem.* 1969, 22, 1779-1782.
Maegawa, T.; Akashi, A.; Esaki, H.; Aoki, F.; Sajiki, H.; Hirota, K. Efficient and Selective Deuteration of Phenylalanine Derivatives Catalyzed by Pd/C. *Synlett* 2005, No. 5, 845-847.
Needleman and Wunsch, A General Method Applicable to the Search for Similarities in the Amino Acid Sequence of Two Proteins, *J. Mol. Biol.*, 48:443, 1970.
Nelson, S. D.; Trager, W. F. The Use of Deuterium Isotope Effects to Probe the Active Site Properties, Mechanism of Cytochrome P450-Catalyzed Reactions, and Mechanisms of Metabolically Dependent Toxicity. *Drug Metab. Dispos.* 2003, 31(12), 1481-1498.
Notredame et al., "T-Coffee: A novel method for multiple sequence alignments," *Journal of Molecular Biology* 302: 205-217, 2000.
Nukuna, B. N.; Goshe, M. B.; Anderson, V. E. Sites of Hydroxyl Radical Reaction with Amino Acids Identified by 2H Nmr Detection of Induced 1H/2H Exchange. *J. Am. Chem. Soc.* 2001, 123 (6), 1208-1214.
Pajk, M.; Pałka, K.; Winnicka, E.; Kańska, M. The Chemo-Enzymatic Synthesis of Labeled 1-Amino Acids and Some of Their Derivatives. *J. Radioanal. Nucl. Chem.* 2018, 317 (2), 643-666.
Pearson and Lipman, Improved tools for biological sequence comparison, *Proc. Natl. Acad. Sci. USA* 85:2444, 1988.
Pirali, T.; Serafini, M.; Cargnin, S.; Genazzani, A. A. Applications of Deuterium in Medicinal Chemistry. *J. Med. Chem.* 2019, 62 (11), 5276-5297.
Rowbotham, J. S.; Ramirez, M. A.; Lenz, O.; Reeve, H. A.; Vincent, K. A. Bringing Biocatalytic Deuteration into the Toolbox of Asymmetric Isotopic Labelling Techniques. *Nat. Commun.* 2020, 11 (1), 1-7.
Sheppard, D.; Li, D. W.; Brüschweiler, R.; Tugarinov, V. Deuterium Spin Probes of Backbone Order in Proteins: 2H NMR Relaxation Study of Deuterated Carbon α Sites. J. Am. Chem. Soc. 2009, 131 (43), 15853-15865.
Smith and Waterman, Comparison of Biosequences, *Adv. Appl. Math.*, 2:482, 1981.
Thielges, M. C.; Case, D. A.; Romesberg, F. E. Carbon-Deuterium Bonds as Probes of Dihydrofolate Reductase. *J. Am. Chem. Soc.* 2008, 130 (20), 6597-6603.
Thompson, C. M.; McDonald, A. D.; Yang, H.; Cavagnero, S.; Buller, A. R. Modular Control of L-Tryptophan Isotopic Substitution via an Efficient Biosynthetic Cascade. *Org. Biomol. Chem.* 2020, 18 (22), 4189-4192.
Thompson J. D., Higgins D. G., Gibson T. J., "CLUSTAL W: improving the sensitivity of progressive multiple sequence alignment through sequence weighting, position-specific gap penalties and weight matrix choice," *Nucleic Acids Research* 22: 4673-4680, 1994.
Voges, R. From Chiral Bromo [$^{13,\ 14}C_n$] Acetyl Sultams to Complex Molecules Singly / Multiply Labelled with Isotopic Carbon. Feb. 2002, No. 867-897.
Wong, C. H.; Whitesides, G. M. Enzyme-Catalyzed Organic Synthesis: Regeneration of Deuterated Nicotinamide Cofactors for Use in Large-Scale Enzymatic Synthesis of Deuterated Substances. *J. Am. Chem. Soc.* 1983, 105 (15), 5012-5014.
Yvon, M.; Chambellon, E.; Bolotin, A.; Roudot-Algaron, F. Characterization and Role of the Branched-Chain Aminotransferase (BcaT) Isolated from *Lactococcus lactis* Subsp. *Cremoris* NCDO 763. *Appl. Environ. Microbiol.* 2000, 66 (2), 571-577.

* cited by examiner

**Biosynthesis of L-*allo*-Ile in *Streptomyces scopuliridis***

L-Ile (9)

10

L-*allo*-Ile (11)

- *Protein-protein interaction enables epimerization of L-Ile*
- *DsaD = aminotransferase, DsaE = partner protein*

Kinetic analysis of Cβ-deuteration of L-Ile

Cβ-deuteration under varied [DsaE]

Kinetic analysis of Cα-deuteration of L-Ile

Proposed mechanism of deuterium incorporation

Optimization of two-protein catalyzed β-deuteration of α-amino acids

SITE-SELECTIVE DEUTERATION OF AMINO ACIDS THROUGH DUAL PROTEIN CATALYSIS

CROSS-REFERENCE TO RELATED APPLICATIONS

Priority is hereby claimed to provisional application Ser. No. 63/317,315, filed Mar. 7, 2022, which is incorporated herein by reference.

FEDERAL FUNDING STATEMENT

This invention was made with government support under GM137417 awarded by the National Institutes of Health. The government has certain rights in the invention.

SEQUENCE LISTING

The instant application contains a Sequence Listing which has been submitted in an XML file with the USPTO and is hereby incorporated by reference in its entirety. The Sequence Listing was created on Feb. 17, 2023, is named "P220181US02-SEQUENCE_LISTING.xml," and is 15,365 bytes in size.

BACKGROUND

Deuterated compounds have received significant attention owing to their unique physical and chemical properties.[1] For example, the deuteration of drug molecules can alter their pharmacokinetic properties by slowing oxidative metabolism of the compound in vivo.[2-4] This change can extend the lifetime of the active pharmaceutical agent and enable lower dosing to achieve the same physiological effects.[2-4] As a result, deuterium isotopologs of several known pharmacophores are currently in clinical trials (such as $d_3$-l-DOPA, and $d_9$-l-868417) or have been fully approved (deutetrabenazine).[3] Other deuterated molecules, such as amino acids, are particularly useful in biochemistry and have been used in evaluating enzyme mechanisms, tracking metabolites through biosynthesis and for improving signal in NMR analysis.[5-8] Control over the site of the modification (Cα or Cβ deuteration) of amino acids is particularly important in protein NMR, enabling the attenuation of specific signals to improve resolution.[8] These applications have spurred strong demand for methods to generate selectively deuterated α-amino acids. However, there are significant synthetic challenges for efficiently accessing isotopologs in a site- and stereoselective manner.

A few general approaches have been developed to access Cα and Cβ deuterated α-amino acids including de novo synthesis from deuterated building blocks or by pre-activation of the amine, followed by non-deuterium hydrogen/deuterium (H/D) exchange under basic conditions.[9-11] Small molecule-based methods that avoid pre-functionalization of amino acids are rare and typically involve catalytic hydrogenation (Pd/C or Pt/C) in $D_2O$.[12,13] This approach has been generally limited to the synthesis of Phe or Tyr isotopologs.[12,13] Amino acids exclusively labeled at Cβ are useful isotopologs for nuclear magnetic resonance (NMR) studies and have been used to probe the enzyme mechanism.[36,37] However, the synthesis of selectively Cβ-deuterated amino acids is particularly challenging and has only been accomplished by multi-step synthesis from selectively deuterated building blocks or by radical deuteration under gamma irradiation conditions.[12-16] These approaches are not general for amino acid substrates, as de novo amino acid synthesis requires unique synthetic routes for each desired product. Direct functionalization of amino acids using radical chemistry has been demonstrated, but site-selectivity is highly substrate-dependent, reducing the appeal of this approach.[15]

The search for techniques to directly and selectively deuterate amino acids has led to the development of several enzymatic and chemoenzymatic processes.[9,17] The three-dimensional architecture of an enzyme active site can provide strong control over the site- and stereo-selectivity of reactions. Enzymes also operate directly on free amino acids, avoiding the need for protecting or directing group strategies and streamlining synthetic routes. Previous chemoenzymatic strategies for amino acid deuteration at Cα and Cβ have proceeded through enzyme-catalyzed deuteride delivery (via NAD(P)D) to achieve reductive amination or through transamination of deuterated α-keto acids.[18-20] Such approaches require the in situ regeneration of deuterated reducing equivalents or pre-functionalization of ketone substrates, which present additional challenges to the reaction design.[18-20] Enzymes that catalyze simple H/D exchange avoid these requirements and efficiently access isotopologs from their proteo-precursors using inexpensive $D_2O$ as the heavy label source. For example, PLP-dependent enzymes that catalyze Cα-deprotonation have been used to generate Cα-deuterated amino acids and esters.[21-23] In a similar fashion, enzymes that catalyze Cα and Cβ deprotonation (such as methionine-γ-lyase and cystathionine-γ-synthase) can generate Cα/Cβ-deuterated products when reactions are performed in $D_2O$.[24-26] These enzymes provide efficient access to isotopologs, but label both Cα and Cβ indiscriminately and have relatively narrow substrate scopes.[24,25] Site-selective Cβ-deuteration remains a challenging pattern to access, and has only been accomplished on aromatic amino acids by the reverse action of phenylalanine ammonia lyase in $D_2O$.[27,28] We envisioned that an operationally-simple enzymatic route to selectively deuterated materials would be attractive to the synthetic community. In particular, we anticipated that the ability to tune the site-selectivity of an H/D exchange reaction would enable efficient synthesis of isotopologs with the desired labeling pattern, precluding the need for amino acid pre-functionalization steps.

Recently, Li et al. elucidated the biosynthetic origins of L-allo-Ile, a non-standard amino acid (nsAA) found in several bacterial peptide natural products.[29] Two biosynthetic proteins were shown to work in tandem to catalyze the epimerization of canonical (2S,3S)-Ile to (2S,3R)-Ile (L-allo-Ile) in *Streptomyces scopuliridis*: (1) DsaD, originally annotated as a PLP-dependent branched chain aminotransferase (BCAT) and (2) DsaE, a small partner protein, which shares very little sequence identity with other known protein families (FIG. 1A).[29] In the absence of either protein, the epimerization reaction was not observed, indicating that epimerization proceeds through a unique, two protein-dependent mechanism. In addition, when DsaD was incubated with α-ketoglutarate and Ile, no aminotransferase activity was observed, indicating an unusual catalytic role for this protein.[29] The epimerization reaction observed by Li et al. was proposed to occur through binding of L-Ile to the PLP cofactor, followed by Cα-deprotonation of L-Ile to form an iminium ion.[29] A second deprotonation was proposed to occur at Cβ to form an achiral enamine intermediate (FIG. 1A).[29] Subsequent reprotonation of Cβ on the opposite face would lead to the observed epimerization and facially selective reprotonation at Cα would deliver L-allo-Ile as the product.[29]

Although a mechanism for the L-Ile (Ile) epimerization reaction was previously proposed, little is known about the role of each protein in this transformation. The practical limitations of studying the Ile epimerization reaction (i.e. the efficient chromatographic separation of diastereomers) present significant roadblocks to a detailed analysis of kinetics and mechanism. In addition, using epimerization as a readout for enzyme activity provides no information about the contributions of each protein to individual steps in the catalytic cycle. For example, must DsaD and DsaE be in complex for substrate binding to occur? Can non-branched amino acids productively enter a catalytic cycle? In the absence of a second stereocenter, any reaction would simply return the starting material and provide no readout of activity.

In the present disclosure, we show that epimerization reactions performed in $D_2O$ lead to H/D exchange at Cα and Cβ of Ile, providing a simple, mass spectrometry-based readout of enzyme activity. This assay can be utilized to probe key features of DsaD/E catalysis and leverage these insights to prepare selectively deuterated amino acids, providing a unique biocatalytic platform to access these important materials. The biocatalytic route for non-deuterium hydrogen-deuterium exchange eliminates the requirement for amine protection and enables direct installation of the deuterium on a free amino acid substrate. The streamlined synthesis of isotopologs minimizes the environmental impacts when compared to traditional synthetic routes while simultaneously reducing the expense of making these molecules. Moreover, this route allows access to exclusively Cβ-deuterated amino acids. Very few methods exist for accessing these molecules.

SUMMARY

As described herein, a dual protein system comprising an aminotransferase and a small partner protein has been harnessed to implement a method for selective Cα and Cβ deuteration of amino acids. Thus, disclosed herein is a method of using the dual protein system and their homologs to produce selectively Cα and/or Cβ deuterated amino acids. More specifically, disclosed herein is a method of making a deuterated amino acid, comprising contacting a non-deuterated amino acid having an α-position carbon atom and a β-position carbon atom with deuterium and a protein selected from the group consisting of an aminotransferase and a combination of an aminotransferase and a partner protein, for a time and at a temperature to selectively deuterate the non-deuterated amino acid at the α-position carbon atom to yield a Cα-deuterated amino acid or to selectively deuterate the non-deuterated at both the α-position and the β-position carbon atom to yield a Cα- and Cβ-deuterated amino acid.

The aminotransferase is a protein comprising an amino acid sequence at least 85% identical to SEQ ID NO: 1 or SEQ ID NO: 2. The partner protein is a protein comprising an amino acid sequence at least 85% identical to SEQ ID NO: 3 or SEQ ID NO: 4.

In some embodiments, the aminotransferase is a protein comprising an amino acid sequence at least 95% identical to SEQ ID NO: 1 or SEQ ID NO: 2. The partner protein is a protein comprising an amino acid sequence at least 95% identical to SEQ ID NO: 3 or SEQ ID NO: 4.

In one version of the method, the non-deuterated amino acid is contacted with the deuterium and the aminotransferase to yield a Cα-deuterated amino acid.

In another version, the non-deuterated amino acid is contacted with the deuterium and the combination of the aminotransferase and the partner protein to yield a Cα- and Cβ-deuterated amino acid.

In another version, the method further comprises contacting the Cα- and Cβ-deuterated amino acid with non-deuterium hydrogen and the aminotransferase, for a time and at a temperature to selectively replace the deuterium at the α-position carbon atom with the non-deuterium hydrogen to yield a Cβ-deuterated amino acid. Preferably, the non-deuterium hydrogen is provided as non-deuterated water.

Preferably, the deuterium is provided as deuterated water.

In some embodiments, the protein used in the method is cell-free protein.

The temperature ranges from about 20° C. to about 40° C.

The time ranges from about 1 hour to about 24 hours.

The objects and advantages of the disclosure will appear more fully from the following detailed description of the preferred embodiment of the disclosure made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A. Steady-state kinetic analysis describing Cβ-deuteration[a] of L-Ile under varied equivalents of partner enzyme DsaE. FIG. 2B. Steady-state kinetic analysis of Cβ-deuteration rates[a] at a constant 1 mM L-Ile, measured against increasing equivalents of DsaE. FIG. 2C. Steady-state kinetic analysis of Cα-deuteration[a] of L-Ile in the presence and absence of partner protein DsaE. FIG. 2D. Proposed mechanism of selective deuterium incorporation at Cα and Cβ catalyzed by dual protein catalysis. FIG. 2E. UV-visible spectrum of DsaD in the absence and presence of L-Ile.[a] Measurement of initial rates was performed in duplicate at 24° C. Conditions: 0.1-10 mM L-Ile, 3 μM DsaD, 50 mM sodium phosphate (pD 8.4), and 0.1 mM PLP in $D_2O$ (99.9%). Proteins were exchanged into a 50 mM sodium phosphate-$D_2O$ (pD 8.4) solution prior to reaction initiation to minimize proton contamination (<1% $H_2O$). Following quench with MeCN, crude reaction products were subjected to functionalization with Marfey's reagent (L-FDAA) to enable analysis by reverse-phase chromatography and quantification of isotope incorporation by mass spectrometry.

FIG. 3A. Optimization of Cβ-deuteration by increasing equivalents of partner protein DsaE. FIG. 3B. Evaluation of substrate scope of dual-protein-catalyzed Cα/Cβ deuteration under optimized conditions. FIG. 3C. UV-visible spectroscopy used to evaluate non-native substrate binding to DsaD. Reaction conditions: 10 mM amino acid substrate, 50 μM DsaE, 5 μM DsaD (10:1), 50 mM sodium phosphate (pD 8.4), 0.1 mM PLP, $D_2O$, 37° C., 8 h. Reactions performed in duplicate, and percentage isotope incorporation is reported as the average of the replicates.

DETAILED DESCRIPTION

Abbreviations and Definitions

Figure 1A:
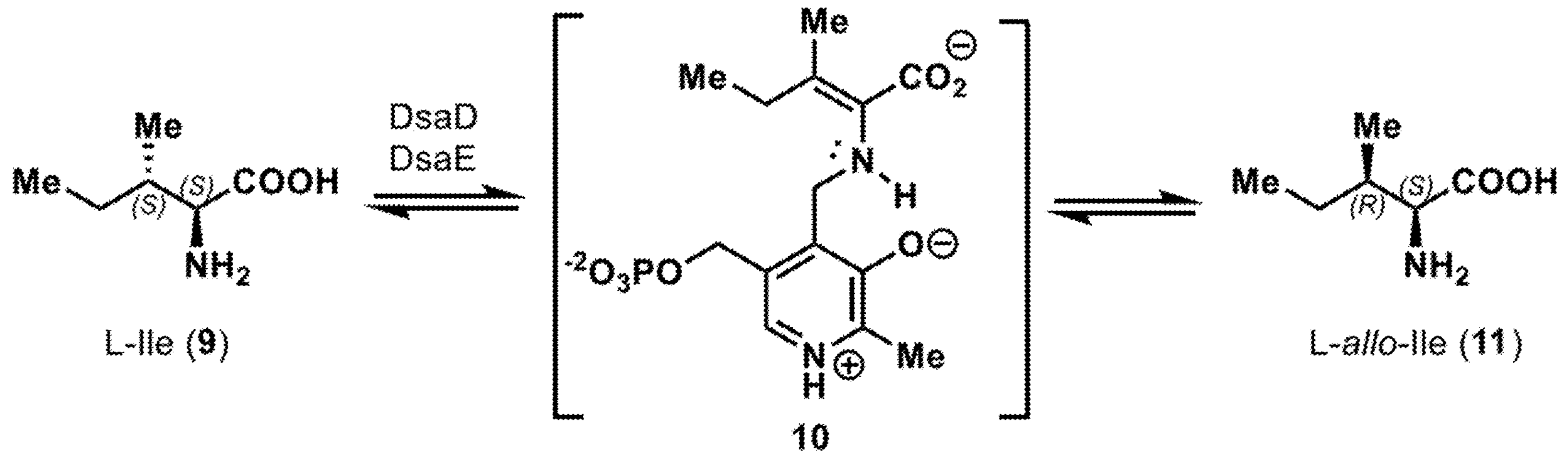
FIG. 1A. Biosynthesis of L-allo-Ile by two-protein catalyzed epimerization of L-Ile.

HR-ESI-MS=high-resolution electrospray ionization mass spectrometry.

NMR=nuclear magnetic resonance spectrometry.

PLP=pyridoxal 5'-phosphate.

UPLC-MS=ultra-high-pressure liquid chromatography-mass spectrometry.

UPLC-DAD-MS=ultra-high-pressure liquid chromatography-mass spectrometry with diode array detection As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the term or value so referenced.

The general term "hydrogen" as used herein refers to any isotope or form of hydrogen, including protium, deuterium, tritium, etc. "Non-deuterium hydrogen" refers to any isotope or form of hydrogen that is not deuterium. In some versions, the non-deuterium hydrogen comprises or consists of protium.

The term "deuterated" used with reference to a single compound or radical (e.g., a single water molecule or a single amino acid) refers to a compound or radical in which one or more hydrogens in the compound or radical is deuterium (e.g., a non-deuterium hydrogen is substituted with deuterium). Deuterated compounds may be mono-substituted, di-substituted, multi-substituted or fully substituted. The terms "one or more deuterated" and "mono- or multi-deuterated" can be used interchangeably. An example of a deuterated compound is $D_2O$.

The term "deuterated" used with reference to a substance refers to a substance in which the deuterium content of the substance is higher than natural isotopic deuterium abundance (about 0.0156% by number of total hydrogen present). "Substance" in this context refers to a collection of multiple copies of a given compound or radical (e.g., a collection of water molecules or a collection of a given type of amino acid). "Deuterium content" as used herein refers to the amount (by number) of deuterium in a substance relative to total hydrogen in the substance. In some versions, the deuterium content of the substance is at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99% or 100%.

Some versions of the invention employ deuterated water. Deuterated water is water (a collection of water molecules) having a deuterium content higher than natural deuterium abundance. In some versions, the deuterium content of the deuterated water is at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 99% or 100%.

The term "non-deuterated" or "undeuterated" used with reference to a single compound or radical (e.g., a water molecule or single amino acid) refers to a compound or radical completely devoid of deuterium.

The term "non-deuterated" or "undeuterated" used with reference to a substance (e.g., a collection of water molecules or a collection of a given type of amino acid) refers to a substance that has a percentage of deuterium atoms not higher than the natural isotopic deuterium content (about 0.0156%). In some versions, the non-deuterated substance has a deuterium content equal to or lower than natural deuterium abundance. In some versions, the deuterium content of the non-deuterated substance is less than 0.0156%, such as less than 0.01%, less than 0.001%, less than 0.0001%, less than 0.00001%, less than 0.000001% or 0%.

Some versions of the invention employ non-deuterated water. Non-deuterated water is water (a collection of water molecules) having a deuterium content equal to or lower than natural deuterium abundance. In some versions, the deuterium content of the deuterated water is less than 0.0156%, such as less than 0.01%, less than 0.001%, less than 0.0001%, less than 0.00001%, less than 0.000001% or 0%. Unless the context clearly dictates otherwise, the terms "water" and "$H_2O$" used without the modifiers "deuterated" or "non-deuterated," refer to non-deuterated water or $H_2O$, respectively.

The term "contacting" refers to the act of touching, making contact, or of bringing to immediate or close proximity, including at the molecular level, for example, to bring about a chemical reaction, or a physical change, e.g., in a solution or in a reaction mixture.

The term "homologous sequences" or "homologs" as used herein refers to a polynucleotide or polypeptide sequence having, for example, about 100%, about 99% or more, about 98% or more, about 97% or more, about 96% or more, about 95% or more, about 94% or more, about 93% or more, about 92% or more, about 91% or more, about 90% or more, about 88% or more, about 85% or more, about 80% or more, about 75% or more, about 70% or more, about 65% or more, about 60% or more, about 55% or more, about 50% or more, about 45% or more, or about 40% or more sequence identity to another polynucleotide or polypeptide sequence when optimally aligned for comparison. In certain versions of the genes and proteins described herein, homologous sequences can retain the same type and/or level of a particular activity of interest. In some versions, homologous sequences have between 85% and 100% sequence identity, whereas in other versions there is between 90% and 100% sequence identity. In particular embodiments, there is between 95% and 100% sequence identity.

The term "homology" refers to sequence similarity or sequence identity. Homology is determined using standard techniques known in the art. (See, for example, Smith and Waterman, *Adv. Appl. Math.,* 2:482, 1981; Needleman and Wunsch, *J. Mol. Biol.,* 48:443, 1970; Pearson and Lipman, *Proc. Natl. Acad. Sci. USA* 85:2444, 1988. See also programs such as GAP, BESTFIT, FASTA, and TFASTA in the Wisconsin Genetics Software Package (Genetics Computer Group, Madison, WI, USA); and Devereux et al., *Nucl. Acid Res.,* 12:387-395, 1984.) A non-limiting example includes the use of the BLAST program (Altschul et al., "Gapped BLAST and PSI-BLAST: a new generation of protein database search programs," *Nucleic Acids Res.* 25:3389-3402, 1997) to identify sequences that can be said to be "homologous." A recent version such as version 2.2.16, 2.2.17, 2.2.18, 2.2.19, or the latest version, including sub-programs such as blastp for protein-protein comparisons, blastn for nucleotide-nucleotide comparisons, tblastn for protein-nucleotide comparisons, or blastx for nucleotide-protein comparisons, and with parameters as follows: Maximum number of sequences returned 10,000 or 100,000; E-value (expectation value) of 1e-2 or 1e-5, word size 3, scoring matrix BLOSUM62, gap cost existence 11, gap cost extension 1, may be suitable. An E-value of 1e-5, for example, indicates that the chance of a homologous match occurring at random is about 1 in 10,000, thereby marking a high confidence of true homology.

The terms "percent sequence identity," "percent amino acid sequence identity," "percent gene sequence identity," and/or "percent polynucleotide sequence identity," with respect to two polypeptides, polynucleotides and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The term "alignment" refers to a method of comparing two or more polynucleotides or polypeptide sequences for the purpose of determining their relationship to each other. Alignments are typically performed by computer programs that apply various algorithms. It is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW, (see, Thompson J. D., Higgins D. G., Gibson T. J., "CLUSTAL W: improving the sensitivity of progressive multiple sequence alignment through sequence weighting, position-specific gap penalties and weight matrix choice," *Nucleic Acids Research* 22: 4673-4680, 1994); CLUSTALV, (see, Larkin M. A., et al., CLUSTALW2, "ClustalW and ClustalX version 2," *Bioinformatics* 23(21): 2947-2948, 2007); Jotun-Hein, Muscle et al., "MUSCLE: a multiple sequence alignment method with reduced time and space complexity," *BMC Bioinformatics* 5: 113, 2004); Mafft, Kalign, ProbCons, and T-Coffee (see Notredame et al., "T-Coffee: A novel method for multiple sequence alignments," *Journal of Molecular Biology* 302: 205-217, 2000). Exemplary programs that implement one or more of the above algorithms include, but are not limited to MegAlign from DNAStar (DNAStar, Inc. Madison, WI, USA), MUSCLE, T-Coffee, CLUSTALX, CLUSTALV, JalView, Phylip, and Discovery Studio from Accelrys (Accelrys, Inc., San Diego, CA, USA). In a non-limiting example, MegAlign is used to implement the CLUSTALW alignment algorithm with the following parameters: Gap Penalty 10, Gap Length Penalty 0.20, Delay Divergent Seqs (30%) DNA Transition Weight 0.50, Protein Weight matrix Gonnet Series, DNA Weight Matrix IUB.

The term "isolated" or "purified" means a material that is removed from its original environment, for example, the natural environment if it is naturally occurring, or a fermentation broth if it is produced in a recombinant host cell fermentation medium. A material is said to be "purified" when it is present in a composition in a higher or lower concentration than the concentration that exists prior to the purification step(s). For example, with respect to a composition normally found in a naturally occurring or wild type organism, such a composition is "purified" when the final composition does not include some material from the original matrix. As another example, where a composition is found in combination with other components in a recombinant host cell fermentation medium, that composition is purified when the fermentation medium is treated in a way to remove some component of the fermentation, for example, cell debris or other fermentation products through, for example, centrifugation or distillation. As another example, a naturally occurring polynucleotide or polypeptide present in a living animal is not isolated, but the same polynucleotide or polypeptide, separated from some or all of the coexisting materials in the natural system, is "isolated," whether such process is through genetic engineering or mechanical separation. Such polynucleotides can be parts of vectors. Alternatively, such polynucleotides or polypeptides can be parts of compositions. Such polynucleotides or polypeptides can be considered "isolated" because the vectors or compositions comprising thereof are not part of their natural environments. In another example, a polynucleotide or protein is said to be purified if it gives rise to essentially one band in an electrophoretic gel or a blot.

The term "amino acid" refers to a group of organic molecules that have a basic amino group ($—NH_2$), an acidic carboxyl group (—COOH), and an organic R group (or side chain) that is unique to each amino acid. The term amino acid is short for α-amino [alpha-amino]carboxylic acid. Each molecule contains a central carbon (C) atom, called the α-carbon (Cα), to which both an amino and a carboxyl group are attached. The remaining two bonds of the α-carbon atom are generally satisfied by a hydrogen (H) atom and the R group. The beta carbon (β-carbon or Cβ) is the first carbon atom of the sidechain (the R group) in an amino acid. All amino acids except for glycine form two stereoisomers that are mirror images of each other. These mirror images are termed enantiomers. The two enantiomers of an amino acid are designated "D" and "L" by reference to their unique optical activities.

Numerical ranges as used herein are intended to include every number and subset of numbers contained within that range, whether specifically disclosed or not. That is, for all purposes, and particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All references to singular characteristics or limitations of the present disclosure shall include the corresponding plural characteristic or limitation, and vice-versa, unless otherwise specified or clearly implied to the contrary by the context in which the reference is made. That is, unless specifically stated to the contrary, "a" and "an" mean "one or more." The phrase "one or more" is readily understood by one of skill in the art, particularly when read in context of its usage.

The systems of the present disclosure can comprise, consist of, or consist essentially of the essential elements and limitations described herein, as well as any additional or optional components, or limitations described herein or otherwise useful in the art. The disclosure provided herein suitably may be practiced in the absence of any element which is not specifically disclosed herein.

Dual Protein System

As described herein, a dual protein system has been harnessed to implement a method for site selective Cα and Cβ deuteration of amino acids. The dual protein reaction system comprises an aminotransferase and a small partner protein.

The aminotransferase may be "DsaD" in the Desotamides (DSA) gene cluster or a homolog thereof. The amino acid sequence of DsaD is SEQ ID NO:1. The aminotransferase may accordingly have an amino acid sequence of SEQ ID NO: 1 or a sequence at least 40%, at least 50%, at least 60%, at least 70%, at least 80%, at least 85%, at least 90%, at least 95%, at least 97%, or at least 99% identical thereto. Sequence alignment revealed that DsaD showed high sequence homology to the well-studied branched-chain aminotransferases (BCATs), and featured the conserved EXGXXNLFXnLXTXnLXGVXR signature motif found in all class-IV aminotransferases (Li et al., *J. Am. Chem. Soc.* 2016, 138 (1): 408-415). DsaD possess the conserved catalytic lysine residue covalently linked to pyridoxal 5'-phosphate (PLP) (Chen et al., *J. Bacteriol.* 2012, 194: 6206), strongly suggesting their PLP-dependent aminotransferase activities.

SEQ ID NO: 1 DsaD, *Streptomyces scopuliridis* SCSIO ZJ46

(SEQ ID NO: 1)

MHIVTTPVARPLTAQERTERCAAPAFGTAFTEHMV

SARWNPEQGWHDAELVPYGPLLLDPATVGLHYGQV

VFEGLKAFRSHTGEVAVFRPDAHAERMRASARRLM

MPEPPEELFLAAVDALVAQDQEWIPDDPGMSLYLR

PILFASERTLALRPAREYRFLLVAFITEGYFGPAQ

RPVRVWVTDEYSRAAAGGTGAAKCAGNYAGSLLAQ

EEAQRKGCDQVVWLDPVERNWVEEMGGMNLFFVYE

AGGSARLVTPPLTGSLLPGVTRDALLRLAPTLGVP

-continued

VSEAPLSLEQWRADCASGAITEVFACGTAARISPV

NEVSTKDGSWTIGAGAPAEGGVAAGEVTGRLSAAL

FGIQRGELPDSHSWMRPVSPARQSAIT

Alternatively, the aminotransferase may be another branched-chain aminotransferase (BCAT). For example, the aminotransferase may be a BCAT having an amino acid sequence of SEQ ID NO: 2 or a sequence at least 40%, at least 50%, at least 60%, at least 70%, at least 80%, at least 85%, at least 90%, at least 95%, at least 97%, or at least 99% identical thereto.

SEQ ID NO: 2 Branched-chain amino acid aminotransferase, *Escherichia coli* BL21 (DE3)

(SEQ ID NO: 2)

MTTKKADYIWFNGEMVRWEDAKVHVMSHALHYGTS

VFEGIRCYDSHKGPVVFRHREHMQRLHDSAKIYRF

PVSQSIDELMEACRDVIRKNNLTSAYIRPLIFVGD

VGMGVNPPAGYSTDVIIAAFPWGAYLGAEALEQGI

DAMVSSWNRAAPNTIPTAAKAGGNYLSSLLVGSEA

RRHGYQEGIALDVNGYISEGAGENLFEVKDGVLFT

PPFTSSALPGITRDAIIKLAKELGIDVREQVLSRE

SLYLADEVFMSGTAAEITPVRSVDGIQVGEGRCGP

VTKRIQQAFFGLFTGETEDKWGWLDQVNQ

The small partner protein may be "DsaE" or a homolog thereof. DsaE is a protein encoded immediately upstream of the dsaD aminotransferase gene in the DSA gene cluster having an amino acid sequence of SEQ ID NO:3. The small partner protein may accordingly have an amino acid sequence of SEQ ID NO: 3 or a sequence at least 40%, at least 50%, at least 60%, at least 70%, at least 80%, at least 85%, at least 90%, at least 95%, at least 97%, or at least 99% identical thereto.

SEQ. ID. NO: 3 DsaE, *Streptomyces scopuliridis* SCSIO ZJ46

(SEQ. ID. NO: 3)

MTESSPTEVNEARVREYYRLVDADDVLGLVSLFAE

DAVYRRPGYEPMRGHTGLTAFYTGERVIESGRHTV

ATVVARGDQVAVNGVFEGVLKDGRQVRLEFADFFL

LNGERRFSRRDTYFFAPLV

Alternatively, the small partner protein may be "MfnH" or a homolog thereof. MfnH is an orthologue of DsaE (42% identity) found in the Marformycins (MFN) cluster. The amino acid sequence of MfnH is SEQ ID NO: 4. Accordingly, the small partner protein may have an amino acid sequence of SEQ ID NO: 4 or a sequence at least 40%, at least 50%, at least 60%, at least 70%, at least 80%, at least 85%, at least 90%, at least 95%, at least 97%, or at least 99% identical thereto.

SEQ ID NO: 4 MfnH, *Streptomyces drozdowiczii*
(SEQ ID NO: 4)

MGRSETIRRYYELVDAADYEAMFRIFCDDLIYERA

GTEPIEGIVEFRHFYLADRKIRSGRHSLDVLIENG

DWVAARGVFTGQLRTGEAVTTRWADFHQFRGEKIW

RRYTYFADQSV

In one version of the disclosure, the aminotransferase is DsaD, and the small partner protein is DsaE. The native mechanism of the enzymes involves a series of proton transfers; either at Cα when DsaD operates alone or at Cα and Cβ when DsaD and DsaE are present together. Specifically, DsaD alone catalyzes H/D exchange at Cα, while DsaD and DsaE form a catalytically-active complex that can perform H/D exchange at Cα and Cβ. The reaction is as follows:

-continued

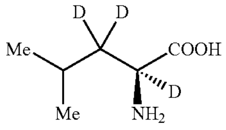

α- and
β-deuteration

Figure 4:
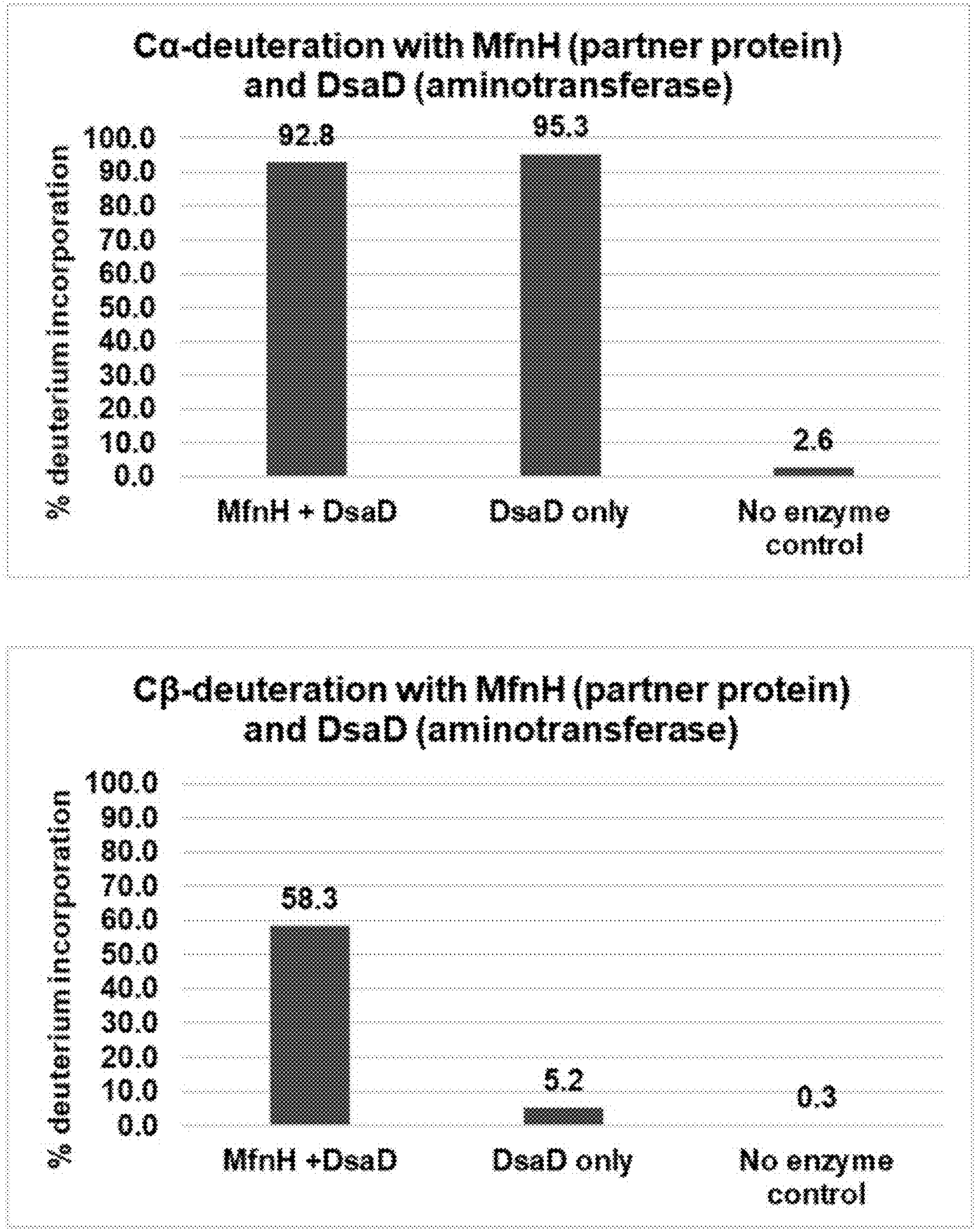
FIG. 4. Deuteration of L-Leu using purified DsaD (5 μM) and MfnH (50 μM) using the described procedure for analytical-scale H/D exchange. Results are reported as the average of 2 trials.

In another version, the small partner protein is MfnH which could also catalyze H/D exchange to generate Cα/β deuterated amino acid. For example, using DsaD as the aminotransferase, MfnH enabled H/D exchange when using both purified protein and clarified lysate. The data for these reactions are shown in FIG. 4 and the Example section. The reaction is as follows:

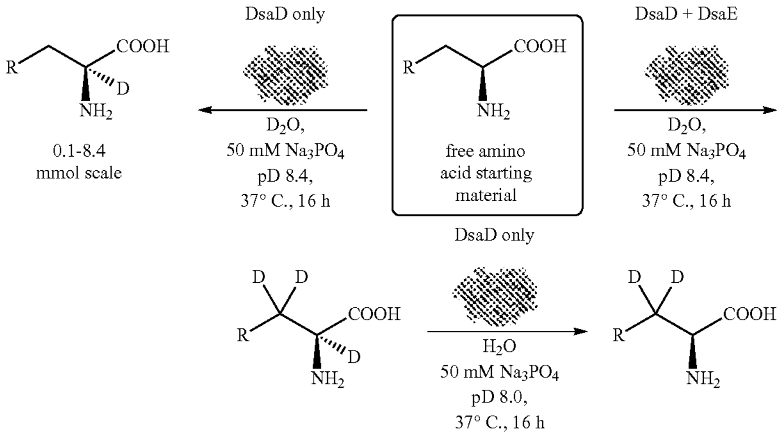

Figure 7:
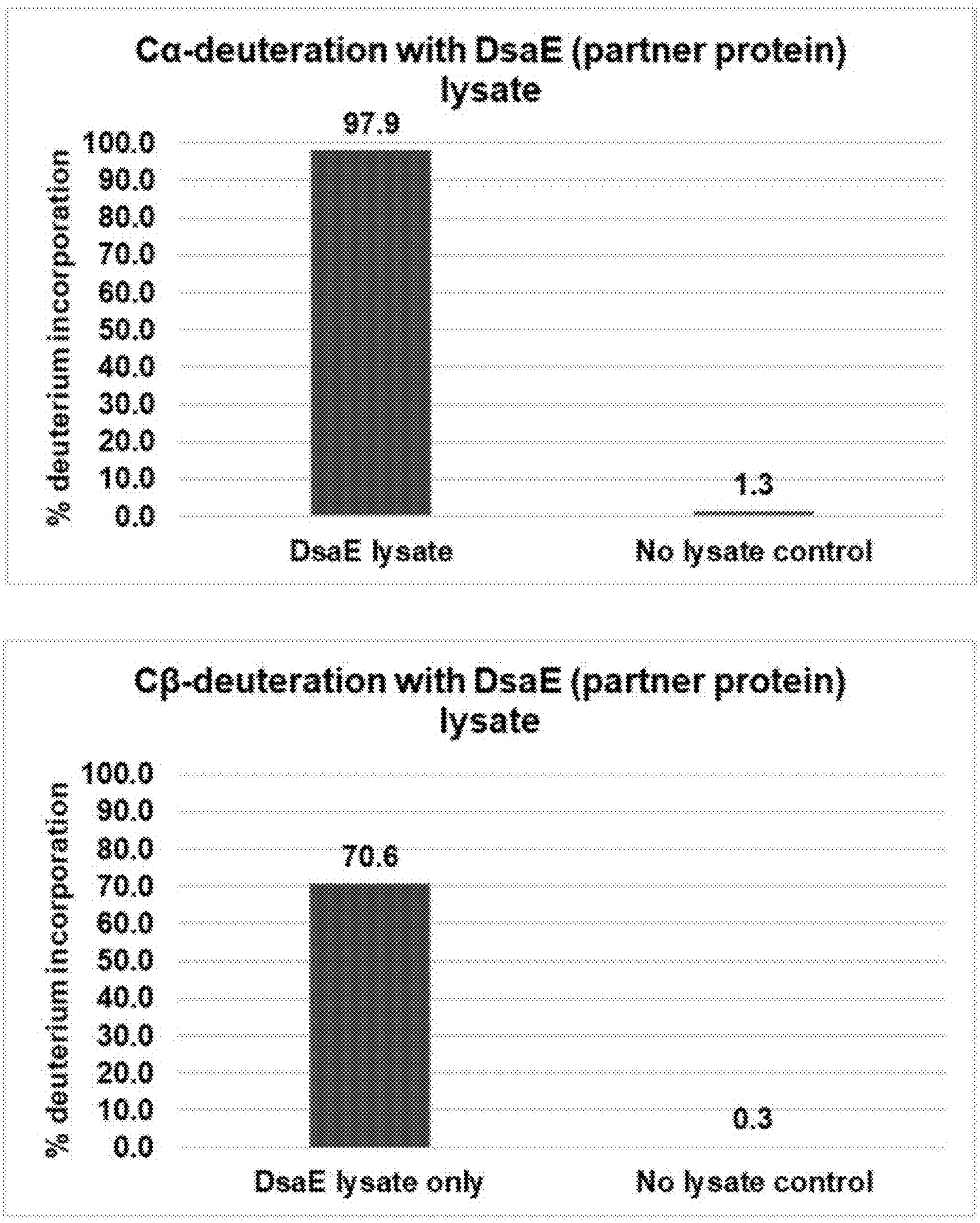
FIG. 7. Deuteration of L-Leu using only DsaE lysate (5% v/v) with minimal $H_2O$ contamination (99.9% D). Reactions were performed using the described procedure for analytical-scale H/D exchange. Results are reported as the average of 3 trials.

In another version, DsaE operates with a BCAT enzyme other than DsaD to effect a Cα/Cβ-exchange. For example, DsaE clarified cell lysates (CCLs) can achieve Cα and Cβ-deuteration without the addition of the aminotransferase DsaD. Instead of relying on DsaD as a partner for catalysis, DsaE promiscuously interacts with native branched-chain amino acid aminotransferases (BCATs) expressed by *E. coli* (SEQ ID NO: 2) for primary metabolism. No overexpression of BCAT is necessary to induce this activity. We simply overexpressed partner protein DsaE and generated a clarified cell lysate from the resulting *E. coli*. The data which demonstrate these results are shown in FIG. 7 and the Example section. The reaction is as follows:

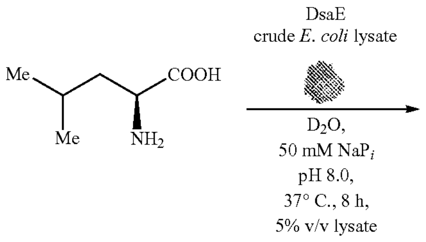

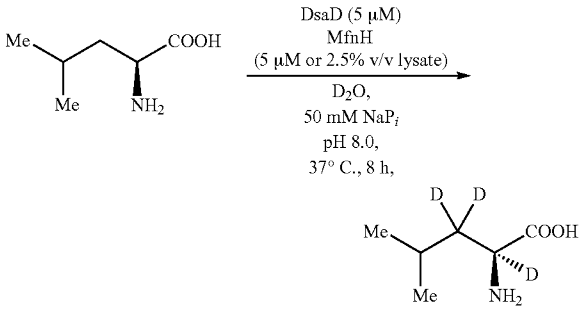

α- and
β-deuteration

Method of Site-Selective Deuteration of Amino Acids

Disclosed herein is a method of making a selectively Cα and/or Cβ deuterated amino acid using the dual protein system. The method comprises contacting a non-deuterated amino acid having an α-position carbon atom and a β-position carbon atom with deuterium and a protein selected from the group consisting of an aminotransferase and a combination of an aminotransferase and a partner protein, for a time and at a temperature wherein the non-deuterated amino acid is selectively deuterated at the α-position carbon atom to yield a Cα-deuterated amino acid or the non-deuterated amino acid is selectively deuterated at both the α-position and the β-position carbon atom to yield a Cα- and Cβ-deuterated amino acid. The method further comprises contacting a Cα- and Cβ-deuterated amino acid with non-deuterium hydrogen and an aminotransferase, for a time and at a temperature wherein the deuterium at the α-position carbon atom is selectively washed out by the non-deuterium hydrogen to yield a Cβ-deuterated amino acid.

In one version, disclosed herein is a method of making a Cα-deuterated amino acid, comprising contacting a non-deuterated amino acid with deuterium and an aminotransferase, for a time and at a temperature wherein the non-deuterated amino acid is selectively deuterated at the α-position carbon atom to yield a Cα-deuterated amino acid.

In another version, disclosed herein is a method of making a Cα- and Cβ-deuterated amino acid, comprising contacting a non-deuterated amino acid with deuterium and a combination of an aminotransferase and a partner protein, for a time and at a temperature wherein the non-deuterated amino acid is selectively deuterated at the α-position and the β-position carbon atom to yield a Cα- and Cβ-deuterated amino acid.

In another version, disclosed herein is a method of making a Cβ-deuterated amino acid, comprising contacting a Cα- and Cβ-deuterated amino acid with non-deuterium hydrogen and an aminotransferase, for a time and at a temperature wherein the deuterium at the α-position carbon atom is selectively washed out by the non-deuterium hydrogen to yield a Cβ-deuterated amino acid. The Cα- and Cβ-deuterated amino acid used herein may be produced by any deuteration methods, including the method described herein using the dual protein system.

The method disclosed herein may be performed in vitro. The aminotransferase or the combination of the aminotransferase and the small partner protein may be prepared by any suitable techniques for preparing active enzymes.

In some embodiments, the proteins are prepared as cell-free proteins. For example, nucleic acids encoding the aminotransferase and the partner protein may be introduced separately or together into the genome of any bacterial strains that can overexpress the enzymes, such as *E. coli*. The overexpressed enzymes may be prepared as cell lysates or further purified by any protein purification processes for use in the method disclosed herein.

The method disclosed herein may be performed in vivo. In some embodiments, the method may be performed by contacting an exogenous amino acid with cells that express the aminotransferase or the combination of the aminotransferase and the small partner protein. In some embodiments, the method may be performed using cells that ectopically express the aminotransferase or the combination of the aminotransferase and the small partner protein.

The method disclosed herein may be used for selective deuteration of a wide range of amino acids, including but not limited to aliphatic amino acids such as isoleucine (Ile), norleucine (Nle), leucine (Leu), norvaline (Nva), and valine (Val); thioether-containing amino acids such as S-methylcysteine (S-Me-Cys) and methionine (Met); aromatic amino acids such as phenylalanine (Phe), tyrosine (Tyr), and tryptophan (Trp); amino alcohols such as homoserine; and amino acids containing amine side chains such as lysine (Lys). In a preferred embodiment, the amino acid is a non-polar amino acid.

When the amino acid is a polar amino acid, such as amino acids with hydroxyl moieties at Cβ, deuteration of the amino acid may be achieved by capping the polar group as an ether. For example, to deuterate threonine (Thr), the amino acid may be modified to methyl-protected Thr (e.g., L-(OMe)-Thr) for contacting with the aminotransferase or the combination of the aminotransferase and the small partner protein.

The following examples are included herein solely to provide a more complete description of the methods disclosed herein. The examples are not intended to limit the scope of the claims in any way.

EXAMPLES

Summary

Figure 1B:
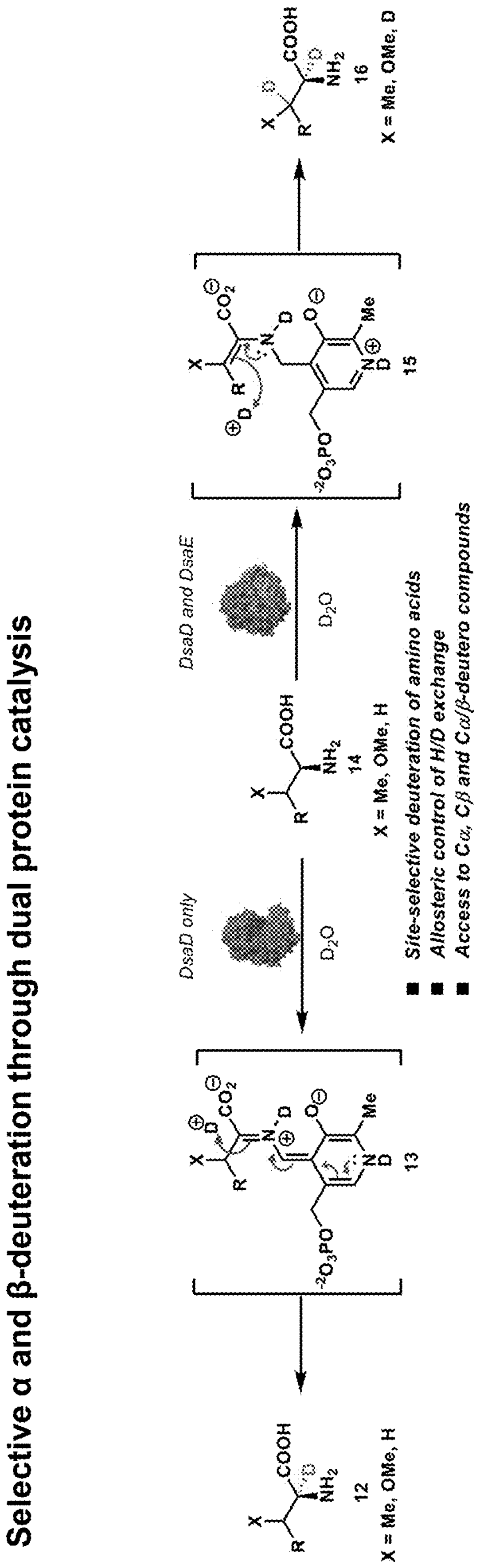
FIG. 1B. Leveraging the Ile epimerization system for selective deuteration of amino acids at Cα and Cβ through dual protein catalysis.

Deuterated amino acids have been recognized for their utility in drug development, for facilitating NMR analysis, and as probes for enzyme mechanism. Small molecule-based methods for the site-selective synthesis of deuterated amino acids typically involve de novo synthesis of the compound from deuterated precursors. In comparison, enzymatic methods for introducing deuterium offer improved efficiency, operating directly on free amino acids to achieve non-deuterium hydrogen-deuterium (H/D) exchange. However, site-selectivity remains a significant challenge for enzyme-mediated deuteration, limiting access to desirable deuteration motifs. Here, we use enzyme-catalyzed deuteration, combined with steady-state kinetic analysis and UV-vis spectroscopy to probe the mechanism of a two-protein system responsible for the biosynthesis of L-allo-Ile. We show that an aminotransferase (DsaD) can pair with a small partner protein (DsaE) to catalyze Cα and Cβ H/D exchange of amino acids, while reactions without DsaE lead exclusively to Cα-deuteration (FIG. 1B). With conditions for improved catalysis, we evaluate the substrate scope for Cα/Cβ-deuteration and demonstrate the utility of this system for preparative-scale, selective labeling of amino acids.

Numbering of compounds in the Examples are shown in bold and correspond to the numbering of compounds in figures.

Methods

General Information

Reagents were purchased from commercial suppliers (Sigma-Aldrich, Bio-Rad) and used without further purification unless otherwise noted. BL21 (DE3) *E. coli* cells were electroporated with a Bio-Rad MicroPulser electroporator at 2500 V. New Brunswick I26R, 120 V/60 Hz shaker incubators (Eppendorf) were used for cell growth. Optical density and UV-vis measurements were collected on a UV-2600 Shimadzu spectrophotometer (Shimadzu). UPLC-MS data were collected on an Acquity UHPLC with an Acquity QDa MS detector (Waters) using an ACQUITY UPLC CSH BEH C18 column (Waters) or an Intrada Amino Acid column (Imtakt). Preparative flash chromatographic separations were performed on an Isolera One Flash Purification system (Biotage). Proton NMR spectra were recorded on a Bruker AVANCE 111-400 MHz spectrometer equipped with a BBFO probe. Proton chemical shifts are reported in ppm (δ) relative to the solvent resonance ($D_2O$, δ 4.79 ppm). Data are reported as follows: chemical shift (multiplicity [singlet (s), doublet (d), doublet of doublets (dd), multiplet (m)], coupling constants [Hz], integration). All NMR spectra were recorded at ambient temperature (about 25° C.).

Plasmid and Protein Information

DsaD, DsaE and MfnH Protein Overexpression: The plasmids containing dsaD, dsaE and mfnH were ordered as a construct in pET-28b(+) from Twist Bioscience (San Francisco, California, USA) and transformed using standard heat-shock protocols for chemically competent *E. coli* into BL21(DE3) cells. Overexpression of these enzymes was achieved using 0.4% glycerol (v/v) Terrific Broth (TB) in 2.8 L flasks. Typically, 1000 mL portions of autoclaved media were inoculated with 5 mL of overnight culture prepared from a single colony in Luria Broth (LB) and 50 µg/mL kanamycin (Gold Biotechnology). Cultures were grown at 37° C. and 200 rpm until the optical density (at 600 nm) reached 0.8. The cultures were then cooled to 4° C. in an ice water bath for 20 min and protein expression was induced with 0.1 mM isopropyl-β-D-1-thiogalactopyranoside (IPTG, Gold Biotechnology, St. Louis, Missouri, USA). Expression was continued at 20° C. overnight (approx. 18 h) at 200 rpm. Cells were then harvested by centrifugation at 4,300×g at 4° C. for 10 min. Codon-optimized nucleotide and amino acid sequences of DsaD, DsaE, and MfnH with 6×His-tag are shown in SEQ ID NOs: 5-10.

Purification of DsaD, DsaE, and MfnH: To purify DsaD, DsaE, and MfnH, cell pellets were thawed on ice and then resuspended in lysis buffer (50 mM sodium phosphate buffer (pH=8.0), 150 mM NaCl) For DsaD, 100 µM pyridoxal 5'-phosphate (PLP) was also added. A solution of 250 mg/mL was generated by the resuspension of cell pellets in 50 mM sodium phosphate buffer at pH 8.0 containing 10 mM imidazole and 1 mg/mL lysozyme. Cells were lysed by sonication of the total cell lysate in 100 mL batches on ice. Each cycle of sonication was 10 s sonication, followed by a 20 s rest period, for a total of 6 min at 60% power. The total cell lysate was centrifuged at 45,000×g for 30 min and the supernatant was removed. The cell lysate was then batch-bound to 3-5 mL of Ni-NTA resin (ThermoFisher Scientific, Waltham, Massachusetts, USA) for 1 h at 4° C. with gentle rocking. The column was washed with 5 column volumes of 20 mM imidazole, 150 mM NaCl, 10% glycerol, 50 mM sodium phosphate buffer (pH=8.0), followed by an additional wash with 40 mM imidazole buffer (containing the same base buffer components). DsaD and DsaE were eluted with 250 mM imidazole, 150 mM NaCl, 10% glycerol, 50 mM sodium phosphate buffer, pH 8.0. The concentrated proteins were desalted using a PD-10 desalting column which was pre-equilibrated with a storage buffer containing 50 mM sodium phosphate (pH 8.0), 150 mM NaCl. The protein was eluted from the column with 3.5 mL of storage buffer, before flash freezing in liquid nitrogen and storage at −80° C. The concentration of DsaD (PLP-dependent) was determined by Bradford assay using bovine serum albumin for a standard concentration curve. The concentration of DsaE was determined by the A280 absorbance method using a Nanodrop spectrophotometer and estimated extinction coefficient from the ProtParam tool on the Expasy server ($\varepsilon$=8940 $M^{-1}cm^{-1}$) (available online from the Swiss Institute of Bioinformatics at the URL expasy.org). Average yield: 60-70 mg/L expression culture for DsaD; 30-40 mg/L expression culture for DsaE and as high as 65 mg/L culture when expression volumes were reduced to 0.5 L. Protein purity was analyzed by sodium dodecyl sulfate-polyacrylamide (SDS-PAGE) gel electrophoresis using 12% polyacrylamide gels.

UV-Vis Spectroscopy: Data were collected between 600 and 300 nm on a UV-2600 Shimadzu spectrophotometer (Shimadzu, Kyoto, Japan) with a semi-micro quartz cuvette (Starna Cells, Atascadero, California, USA) at 25° C. DsaD stock solutions were diluted to 20 µM in 50 mM sodium phosphate pH 8.0. For observation of substrate binding, amino acids were added at concentrations ranging from 2.5-10 mM. Spectra from 600-300 nm were collected after a 2-minute incubation period. Amino acid stocks were prepared as 100 mM stocks in deionized water.

Biocatalytic Reaction Procedures

Stock solutions: Stock solutions of each amino acid (100 mM) were prepared by dissolving the pre-weighed solid with $D_2O$ or $CD_3OD$. $Na_3PO_4$ buffer in $D_2O$ (pD 8.4, 250 mM stock) was prepared by lyophilization of a 250 mM, pD 8.4 buffer pre-made in $dH_2O$.[1] Following lyophilization, the buffer salts were redissolved in $D_2O$ to reduce proton contamination in reactions.

General procedure analytical scale deuteration reactions: α/β deuteration reactions were performed as follows. A 1 mL Eppendorf tube was charged with amino acid (10-20 mM final concentration), $Na_3PO_4$ buffer pD 8.4 (50 mM final concentration), PLP (100 µM final concentration), purified enzymes or appropriate lysate and $D_2O$ and to the appropriate final volume (typically 50 µL). Reactions were carried out at 37° C. for 8 h and quenched by the addition of 3 volumes of acetonitrile. Precipitated biomolecules were pelleted by centrifugation (16,000×g, 10 min) and samples were processed as described below.

Marfey's derivatization of analytical scale reactions: Derivatization of the resulting analytical scale product mixture (to increase overall signal and enable reverse phase chromatographic analysis) was achieved by treatment with Marfey's reagent[2] (1-fluoro-2-4-dinitrophenyl-5-L-alanine amide, L-FDAA) using the following protocol. 25 µL of quenched reaction mix (final amine concentration, 1.6 mM) was added to an Eppendorf tube with 50 µL of 15 mM $NaHCO_3$ (final concentration, 5 mM) and 75 µL of 5 mM L-FDAA (final concentration, 2.5 mM). Derivatization reactions were carried out for 10-12 h before quenching with 150 µL of 60 mM HCl dissolved in acetonitrile. Final reaction analysis was carried out by UPLC-DAD-MS and quantitation as described below.

Quantitation of deuteration in analytical scale reactions: Deuteration reactions were analyzed by UPLC-DAD-MS with single ion recording (SIR) channels set to record a spectrum with the appropriate isotopic mass in positive mode. The area under the curve of recorded SIR peaks was obtained and normalized to account for natural isotopic abundance distributions (e.g. $^{13}C$, $^{15}N$, $^{2}H$, $^{34}S$, etc). Percent deuterium incorporation was calculated by the formula below. These measurements were carried out in an iterative fashion to measure Cα deuteration and Cβ deuteration.

$$\%\ \text{isotope incorporation} = \frac{\text{normalized } AUC \text{ for single isotope mass}}{\text{sum of normalized } AUCs \text{ for all isotope masses}} * 100\%$$

Kinetic analysis of biocatalytic L-Ile deuteration: Initial rates of α- or β-deuteration were obtained by means of end-point assay using the quantitation protocol for analytical scale reactions as described above. All reagents were prepared in $D_2O$ (99.9% D) and protein stocks were dialyzed (3 exchanges over 3 h at 4° C.) into 50 mM sodium phosphate buffer dissolved in $D_2O$ (pD 8.4) using a slide-a-lyzer device with a 3,000 Da cutoff. Reactions were performed at 25° C. in 1 mL Eppendorf tubes. Michaelis constants ($K_M$) for α- and β-deuteration of L-Ile were determined using the concentration range of 0.1-10 mM L-Ile using 3 µM DsaD. Partner protein (DsaE) concentrations were consistent within each experiment and separate experiments were performed using varied equivalents of partner protein (0-50 equiv). Initial velocities were measures in duplicate or triplicate for at least 6 different substrate concentrations for each set of conditions tested. Measurements of the impact of partner protein (DsaE) concentration on the initial rate of β-deuteration were carried out using 1 mM L-Ile, 3 μM DsaD and varying DsaE concentrations between 3 μM-600 μM (1-200 equiv). Under the minimal proton contamination conditions of this assay (99.9% $D_2O$), Cα and Cβ deuteration are assumed to have occurred without back transfer to proton. The data were fit using the Michaelis-Menten equation implemented in Prism.

Preparation of clarified lysates (DsaD, DsaE and MfnH): 30 g of cell pellet containing DsaD or DsaE or MfnH was resuspended to a volume of 45 mg/mL in lysis buffer containing 50 mM $Na_3PO_4$ (pH 8.0), 10% glycerol and 150 mM NaCl. Cells were lysed by sonication of the total cell lysate in 100 mL batches on ice. Each cycle of sonication was 10 s sonication, followed by a 20 s rest period, for a total of 6 min at 30% power. The total cell lysate was centrifuged at 45,000×g for 20 min and the supernatant was removed. Aliquots of lysate were flash frozen in liquid nitrogen and stored at −80° C. until needed.

Exchange of DsaD and DsaE into $D_2O$—$Na_3PO_4$ buffer system: When necessary, clarified lysates and purified proteins were exchanged into a $D_2O$-based buffer system containing 50 mM $Na_3PO_4$ (–) using a Slide-A-Lyzer MINI dialysis device (ThermoFisher) with a 3 KDa cutoff. A maximum of 500 μL of lysate or protein was added to the device and exchanged 3 times into the $D_2O$ buffer at 4° C. before setting up reactions.

General procedure for milligram-scale biocatalytic deuteration: A 4-dram scintillation vial was charged with amino acid (10-20 mM final concentration), $Na_3PO_4$ buffer pD 8.4 (50 mM final concentration), PLP (100 μM final concentration), DsaD clarified cell lysate (2.5% v/v), DsaE clarified cell lysate (if applicable) (2.5% v/v), and $D_2O$ (or $dH_2O$) to the appropriate final volume. The reaction vessel was placed in an incubator at 37° C. for 16 h. Reaction progress was monitored by UPLC-MS. After reaction completion, the reaction mixture was quenched with an equivalent volume of acetone and centrifuged (4,000 rpm, 10 min) to remove denatured protein. Supernatant was transferred to a clean beaker, the decanted supernatant was concentrated to remove acetone by rotary evaporation and loaded onto a preparative reverse-phase C18 column pre-equilibrated with water. Purification was performed via gradient elution on an Isolera One Flash Purification system (Biotage). Fractions bearing product (confirmed by UPLC-MS sampling of fraction tubes) were pooled and dried by rotary evaporation. The product was then resuspended in a minimal quantity of water, transferred to a pre-weighed 20 mL vial, frozen, and lyophilized.

Preparative Scale Synthesis of Deuterated Amino Acids

49

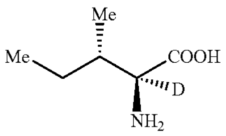

L-isoleucine-2-d (45)

L-Ile was dissolved in $D_2O$ (25 mg, 0.19 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v) and $D_2O$ to a final volume of 9.53 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (21.3 mg isolated, 84%). $^1H$ NMR (400 MHz, $D_2O$) δ 1.96 (dqd, $J_{H-H}$=9.3 Hz, 7.0 Hz, 4.8 Hz, 1H), 1.53-1.38 (m, 1H), 1.32-1.17 (m, 1H), 0.99 (d, $J_{H-H}$=7.0 Hz, 3H), 0.92 (t, $J_{H-H}$=7.4 Hz, 3H); HR-ESI-MS: m/z calcd for $C_6H_{12}DNO_2$ $[M-H]^-$: 131.0936. found: 131.0936.

50

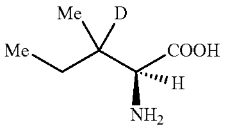

L-isoleucine-3-d (46)

A crude reaction mixture containing L-Ile-2,3-$d_2$ was dissolved in $dH_2O$ (30 mg, 0.19 mmoles, 10 mM final concentration) and combined with $Na_3PO_4$ pD 8.4 (250 mM stock dissolved in $dH_2O$, 50 mM final concentration), PLP (20 mM stock dissolved in $dH_2O$, 100 μM final concentration), DsaD crude cell lysate (2.5% v/v) and $dH_2O$ to a final volume of 9.53 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (9.3 mg isolated, 30%). $^1H$ NMR (400 MHz, $D_2O$) δ 3.68-3.34 (m, 1H), 1.49-1.02 (m, 2H), 1.00-0.68 (m, 6H); HR-ESI-MS: m/z calcd for $C_6H_{12}DNO_2$ $[M-H]^-$: 131.0936. found: 131.0936.

23

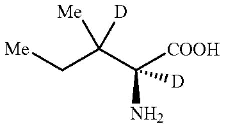

L-isoleucine-2,3-$d_2$ (26)

L-Ile was dissolved in $D_2O$ (25 mg, 0.19 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v), DsaE crude cell lysate (2.5% v/v) and $D_2O$ to a final volume of 9.53 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (23.4 mg isolated, 92%). $^1H$ NMR (400 MHz, $D_2O$) δ 1.50-1.16 (m, 2H), 1.03-0.82 (m, 6H); HR-ESI-MS: m/z calcd for $C_6H_{11}D_2NO_2$ $[M-H]^-$: 132.0999. found: 132.0999.

51

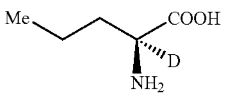

L-norvaline-2-d (47)

L-Nva was dissolved in $D_2O$ (30 mg, 0.25 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v) and $D_2O$ to a final volume of 11.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (6.3 mg isolated, 21%). $^1H$ NMR (400 MHz, $D_2O$) δ 1.79-1.58 (m, 2H), 1.36-1.18 (m, 2H), 0.84 (t, $J_{H-H}$=7.3 Hz, 3H); HR-ESI-MS: m/z calcd for $C_5H_{10}DNO_2$ $[M-H]^-$: 117.0779. found: 117.0779.

52

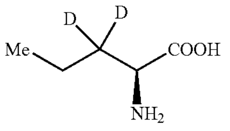

L-norvaline-3,3-$d_2$ (48)

A crude reaction mixture containing L-Nva-2,3,3-$d_3$ was dissolved in $dH_2O$ (6.8 mg, 0.06 mmoles, 20 mM final concentration) and combined with $Na_3PO_4$ pD 8.4 (250 mM stock dissolved in $dH_2O$, 50 mM final concentration), PLP (20 mM stock dissolved in $dH_2O$, 100 μM final concentration), DsaD crude cell lysate (2.5% v/v) and $dH_2O$ to a final volume of 2.91 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (2.6 mg isolated, 39%). $^1H$ NMR (400 MHz, $D_2O$) δ 3.68 (tt, $J_{H-H}$=6.5 Hz, 4.3 Hz, 1H), 1.25 (d, $J_{H-H}$=7.3 Hz, 1H), 0.91-0.76 (m, 3H); HR-ESI-MS: m/z calcd for $C_5H_9D_2NO_2$ $[M-H]^-$: 118.0843. found: 118.0843.

26

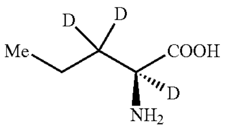

L-norvaline-2,3,3-$d_3$ (27)

L-Nva was dissolved in $D_2O$ (30 mg, 0.25 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v), DsaE crude cell lysate (2.5% v/v) and $D_2O$ to a final volume of 11.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution.

For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (27 mg isolated, 88%). 1H NMR (400 MHz, $D_2O$) δ 1.26 (d, $J_{H-H}$=8.0 Hz, 2H), 0.90-0.77 (m, 3H); HR-ESI-MS: m/z calcd for $C_5H_8D_3NO_2$ $[M-H]^-$: 119.0905. found: 119.0906.

57

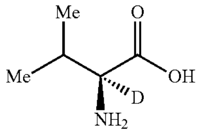

L-valine-2-d (53)

L-Val was dissolved in $D_2O$ (30 mg, 0.25 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v) and $D_2O$ to a final volume of 11.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (25.5 mg isolated, 84%). $^1$H NMR (400 MHz, $D_2O$) δ 2.12 (hept, $J_{H-H}$=7.0 Hz, 1H), 1.00-0.78 (m, 6H); HR-ESI-MS: m/z calcd for $C_5H_{10}DNO_2$ $[M-H]^-$: 117.0779. found: 117.0779.

31

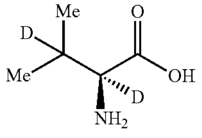

L-valine-2,3-$d_2$ (31)

A crude reaction mixture containing L-Val was dissolved in $D_2O$ (30 mg, 0.25 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v), DsaE crude cell lysate (2.5% v/v) and $D_2O$ to a final volume of 11.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (17.1 mg isolated, 56%). $^1$H NMR (400 MHz, $D_2O$) δ 0.91 (s, 3H), 0.86 (d, $J_{H-H}$=2.4 Hz, 3H); HR-ESI-MS: m/z calcd for $C_5H_9D_2NO_2$ $[M-H]^-$: 118.0843. found: 118.0843.

42

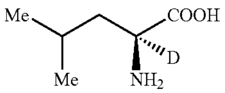

L-leucine-2-d (42)

L-Leu was dissolved in $D_2O$ (30 mg, 0.228 mmoles, 10 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v) and $D_2O$ to a final volume of 11.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (14 mg isolated, 46%). $^1$H NMR (400 MHz, $D_2O$) δ 1.65-1.50 (m, 3H), 0.84 (t, $J_{H-H}$=5.5 Hz, 6H); HR-ESI-MS: m/z calcd for $C_6H_{12}DNO_2$ $[M+H]^+$: 133.1082. found: 133.1081.

25

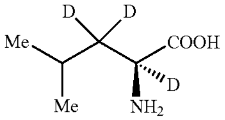

L-leucine-2,3,3-$d_3$ (25)

L-Leu was dissolved in $D_2O$ (30 mg, 0.228 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v), DsaE crude cell lysate (2.5% v/v) and $D_2O$ to a final volume of 11.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (27 mg isolated, 88%). 1H NMR (400 MHz, $D_2O$) δ 1.78-1.57 (m, 1H), 0.94 (dd, $J_{H-H}$=6.5 Hz, 4.8 Hz, 6H); HR-ESI-MS: m/z calcd for $C_6H_{10}D_3NO_2$ $[M-H]^-$: 133.1062. found: 133.1062.

44

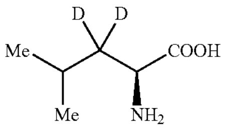

L-leucine-3,3-$d_2$ (44)

A crude reaction mixture containing L-Leu-2,3,3-$d_3$ was dissolved in $dH_2O$ (20 mg, 0.17 mmoles, 20 mM final concentration) and combined with $Na_3PO_4$ pD 8.4 (250 mM stock dissolved in $dH_2O$, 50 mM final concentration), PLP (20 mM stock dissolved in $dH_2O$, 100 μM final concentration), DsaD crude cell lysate (2.5% v/v) and $dH_2O$ to a final volume of 7.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (10.3 mg isolated, 52%). $^1H$ NMR (400 MHz, $D_2O$) δ 3.57 (d, $J_{H-H}$=5.5 Hz, 1H), 1.58 (t, $J_{H-H}$=6.6 Hz, 1H), 0.84 (dd, $J_{H-H}$=6.5 Hz, 4.7 Hz, 6H); HR-ESI-MS: m/z calcd for $C_6H_{11}D_2NO_2$ $[M+H]^+$: 134.1145. found: 134.1144.

53

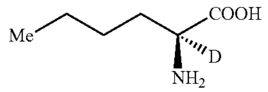

L-norleucine-2-d (49)

L-Nle was dissolved in $D_2O$ (30 mg, 0.228 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v) and $D_2O$ to a final volume of 11.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (19.3 mg isolated, 64%). $^1H$ NMR (400 MHz, $D_2O$) δ 1.84-1.58 (m, 1H), 1.34-1.09 (m, 5H), 0.9-0.69 (m, 4H); HR-ESI-MS: m/z calcd for $C_6H_{12}DNO_2$ $[M-H]^-$: 131.0936. found: 131.0936.

24

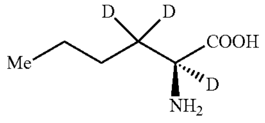

L-norleucine-2,3,3-$d_3$ (24)

L-Nle was dissolved in $D_2O$ (30 mg, 0.228 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v), DsaE crude cell lysate (2.5% v/v) and $D_2O$ to a final volume of 11.4 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (12.8 mg isolated, 42%). $^1H$ NMR (400 MHz, $D_2O$) δ 1.33 (dtd, $J_{H-H}$=8.9 Hz, 5.5 Hz, 2.0 Hz, 3H), 0.99-0.75 (m, 2H); HR-ESI-MS: m/z calcd for $C_6H_{10}D_3NO_2$ $[M-H]^-$: 133.1062. found: 133.1062.

54

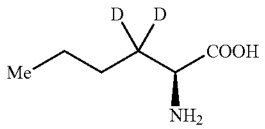

L-norleucine-3,3-$d_2$ (50)

A crude reaction mixture containing L-Nle-2,3,3-$d_3$ was dissolved in $D_2O$ (12.8 mg, 0.097 mmoles, 20 mM final concentration) and combined with $Na_3PO_4$ pD 8.4 (250 mM stock dissolved in $dH_2O$, 50 mM final concentration), PLP (20 mM stock dissolved in $dH_2O$, 100 μM final concentration), DsaD crude cell lysate (2.5% v/v), and $dH_2O$ to a final volume of 4.85 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (6.4 mg isolated, 50%). $^1$H NMR (400 MHz, $D_2O$) δ 3.56 (d, $J_{H-H}$=4.7 Hz, 1H), 1.84-1.61 (m, 1H), 1.24 (dtd, $J_{H-H}$=8.1 Hz, 4.3 Hz, 1.7 Hz, 5H), 0.88-0.72 (m, 4H); HR-ESI-MS: m/z calcd for $C_6H_{11}D_2NO_2$ $[M-H]^-$: 132.0999. found: 132.0999.

59

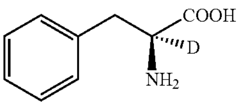

L-phenylalanine-2-d (55)

L-Phe was dissolved in $D_2O$ (30 mg, 0.182 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v) and $D_2O$ to a final volume of 9.08 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (22.4 mg isolated, 74%). $^1$H NMR (400 MHz, $D_2O$) δ 7.40-7.04 (m, 5H), 3.18-2.75 (m, 2H); HR-ESI-MS: m/z calcd for $C_9H_{10}DNO_2$ $[M-H]^-$: 165.0779. found: 165.0777.

32

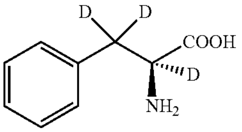

L-phenylalanine-2,3,3-d3 (32)

L-Phe was dissolved in $D_2O$ (30 mg, 0.182 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v), DsaE crude cell lysate (2.5% v/v) and $D_2O$ to a final volume of 9.08 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (17.7 mg isolated, 58%). $^1$H NMR (400 MHz, $D_2O$) δ 7.47 (m, 5H), 3.16 (d, $J_{H-H}$=14.0 Hz, 0.45H), 3.07-2.92 (m, 0.65H); HR-ESI-MS: m/z calcd for $C_9H_8D_3NO_2$ $[M-H]^-$: 167.0905. found: 167.0905.

60

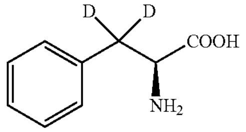

L-phenylalanine-3,3-d2 (56)

A crude reaction mixture containing L-Phe-2,3,3-$d_3$ was dissolved in $dH_2O$ (10 mg, 0.06 mmoles, 20 mM final concentration) and combined with $Na_3PO_4$ pD 8.4 (250 mM stock dissolved in $dH_2O$, 50 mM final concentration), PLP (20 mM stock dissolved in $dH_2O$, 100 μM final concentration), DsaD crude cell lysate (2.5% v/v) and $dH_2O$ to a final volume of 2.99 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (6.2 mg isolated, 63%). $^1$H NMR (400 MHz, $D_2O$) δ 7.44-7.13 (m, 5H), 3.85 (d, $J_{H-H}$=2.2 Hz, 1H), 3.24-2.95 (m, 1H); HR-ESI-MS: m/z calcd for $C_9H_9D_2NO_2$ $[M-H]^-$: 166.0843. found: 166.0840.

58

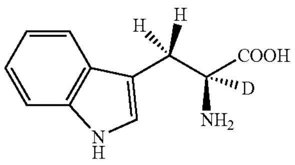

L-tryptophan-2-d (54)

L-Tyr was dissolved in $D_2O$ (30 mg, 0.147 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v), DsaE crude cell lysate (2.5% v/v) and $D_2O$ to a final volume of 7.34 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (26 mg isolated, 86%). $^1$H NMR (400 MHz, $D_2O$) δ 7.62 (dt, $J_{H-H}$=7.9 Hz, 1.0 Hz, 1H), 7.42 (dt, $J_{H-H}$=8.3 Hz, 1.0 Hz, 1H), 7.25-7.13 (m, 2H), 7.08 (ddd, $J_{H-H}$=8.0 Hz, 7.1 Hz, 1.1 Hz, 1H), 3.32 (dd, $J_{H-H}$=15.1 Hz, 5.1 Hz, 1H), 3.14 (dd, $J_{H-H}$=15.1 Hz, 6.4 Hz, 1H); HR-ESI-MS: m/z calcd for $C_{11}H_{11}DN_2O_2$ $[M-H]^-$: 204.0888. found: 204.0888.

61

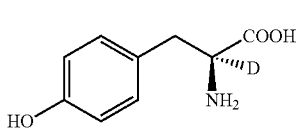

L-tyrosine-2-d (57)

L-Tyr was dissolved in $D_2O$ (30 mg, 0.17 mmoles, 10 mM final concentration) and combined with $Na_3PO_4$ pD 8.4 (250 mM stock dissolved in $D_2O$, 50 mM final concentration), PLP (20 mM stock dissolved in $CD_3OD$ 100 μM final concentration), DsaD crude cell lysate (2.5% v/v) and $D_2O$ to a final volume of 16.56 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (12.9 mg isolated, 43%). $^1$H NMR (400 MHz, $D_2O$) δ 7.04 (d, $J_{H-H}$=8.6 Hz, 2H), 6.74 (d, $J_{H-H}$=8.6 Hz, 2H), 3.03 (d, $J_{H-H}$=14.6 Hz, 1H), 2.88 (d, $J_{H-H}$=14.5 Hz, 1H); HR-ESI-MS: m/z calcd for $C_9H_{10}DNO_3$ $[M-H]^-$: 181.0729. found: 181.0728.

33

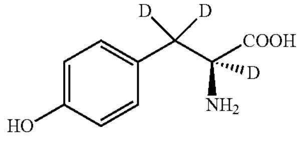

L-tyrosine-2,2,3-$d_3$ (33)

L-Tyr was dissolved in $CD_3OD$ (30 mg, 0.17 mmoles, 10 mM final concentration) and combined with $Na_3PO_4$ pD 8.4 (250 mM stock dissolved in $D_2O$, 50 mM final concentration), PLP (20 mM stock dissolved in $D_2O$ 100 μM final concentration), DsaD crude cell lysate (2.5% v/v), DsaE crude cell lysate (2.5% v/v) and $D_2O$ to a final volume of 16.56 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (11.6 mg isolated, 38%). $^1$H NMR (400 MHz, $D_2O$) δ 7.18 (d, $J_{H-H}$=8.6 Hz, 2H), 6.93-6.85 (m, 2H), 3.19 (d, $J_{H-H}$=14.8 Hz, 0.64H), 3.05 (d, $J_{H-H}$=13.5 Hz, 0.94H); HR-ESI-MS: m/z calcd for $C_9H_8D_3NO_3$ $[M-H]^-$: 183.0854. found: 183.0859.

62

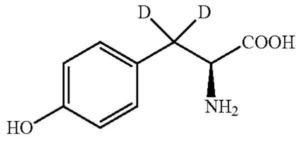

L-tyrosine-3,3-$d_2$ (58)

A crude reaction mixture containing L-Tyr-2,3,3-$d_3$ was dissolved in methanol (12 mg, 0.07 mmoles, 10 mM final concentration) and combined with $Na_3PO_4$ pD 8.4 (250 mM stock dissolved in $dH_2O$, μmM final concentration), PLP (20 mM stock dissolved in $dH_2O$, 100 μM final concentration), DsaD crude cell lysate (2.5% v/v) and $dH_2O$ to a final volume of 16.56 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (3 mg isolated, 25%). $^1$H NMR (400 MHz, $D_2O$) δ 7.08 (d, $J_{H-H}$=8.2 Hz, 2H), 6.76 (d, $J_{H-H}$=8.0 Hz, 2H), 3.65 (t, $J_{H-H}$=6.4 Hz, 1H), 3.05-2.93 (m, 0.59H), 2.85 (dd, $J_{H-H}$=14.2 Hz, 7.5 Hz, 0.87H); HR-ESI-MS: m/z calcd for $C_9H_9D_2NO_3$ $[M-H]^-$: 182.0792. found: 182.0792.

55

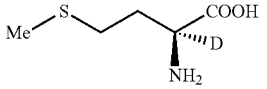

L-methionine-2-d (51)

L-Met was dissolved in $D_2O$ (30 mg, 0.20 mmoles, 20 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v) and $D_2O$ to a final volume of 10.05 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (16.1 mg isolated, 53%). $^1H$ NMR (400 MHz, $D_2O$) δ 2.58-2.43 (m, 2H), 2.12-1.87 (m, 5H); HR-ESI-MS: m/z calcd for $C_5H_{10}DNO_2S$ $[M-H]^-$: 149.0501. found: 149.0501.

29

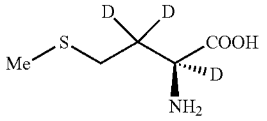

L-methionine-2,3,3-$d_3$ (29)

L-Met was dissolved in $D_2O$ (30 mg, 0.20 mmoles, 10 mM final concentration) and combined with $Na_3PO_4$ pD 8.4 (250 mM stock dissolved in $D_2O$, 50 mM final concentration), PLP (20 mM stock dissolved in $D_2O$, 100 μM final concentration), DsaD crude cell lysate (2.5% v/v), DsaE crude cell lysate (2.5% v/v) and $D_2O$ to a final volume of 20.1 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (8 mg isolated, 26%). 1H NMR (400 MHz, $D_2O$) δ 2.69-2.55 (m, 2H), 2.12 (s, 3H); HR-ESI-MS: m/z calcd for $C_5H_8D_3NO_2S$ $[M-H]^-$: 151.0626. found: 151.0611.

56

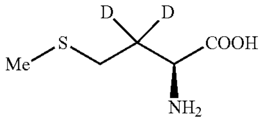

L-methionine-3,3-$d_2$ (52)

A crude reaction mixture containing L-Met-2,3,3-$d_3$ was dissolved in $dH_2O$ (8 mg, 0.05 mmoles, 20 mM final concentration) and combined with $Na_3PO_4$ pD 8.4 (250 mM stock dissolved in $dH_2O$, 50 mM final concentration), PLP (20 mM stock dissolved in $dH_2O$, 100 μM final concentration), DsaD crude cell lysate (2.5% v/v) and $dH_2O$ to a final volume of 2.65 mL. The reaction mixture was incubated overnight at 37° C. and then quenched by the addition of 1 volume acetone. The concentrated solution was transferred to a 50 mL falcon tube and centrifuged at 4,000×g for 10 min to pellet insoluble protein components. The supernatant was transferred to a 250 mL round bottom flask and concentrated by rotary evaporation to remove acetone, leaving the amino acid dissolved in an aqueous solution. For purification, the concentrated reaction mixture was loaded onto a Biotage SNAP Ultra 12 g C18 column and purified on a Biotage flash purification system using a water/methanol gradient. Fractions were analyzed by UPLC-MS to identify product containing fractions. All product containing fractions from purification were then pooled, concentrated by rotary evaporation, and dried via lyophilization, yielding a white solid (3 mg isolated, 38%). $^1H$ NMR (400 MHz, $D_2O$) δ 3.65-3.58 (m, 1H), 2.56-2.46 (m, 2H), 2.02 (s, 3H); HR-ESI-MS: m/z calcd for $C_5H_9D_2NO_2S$ $[M-H]^-$: 150.0563. found: 150.0562.

Results and Discussion

To answer outstanding mechanistic questions about the two protein-dependent epimerization of Ile, we sought a simple, efficient, and reproducible assay for measuring enzyme activity. We envisioned that running the Ile epimerization reaction in $D_2O$ would lead to non-deuterium hydrogen-deuterium (H/D) exchange, which would be used to resolve distinct proton transfer steps in the mechanism. According to the mechanism of Li et al.,[29] reactions of the DsaD/E complex with L-Ile in $D_2O$ would deliver a mixture of Cα and Cβ-deuterated $d_2$-2,3-L-Ile and $d_2$-2,3-L-allo-Ile (23). To ease chromatographic challenges with highly polar amino acids, reactions were quenched and the crude reaction was treated with Marfey's reagent (L-FDAA).[30] Reactions were analyzed by mass spectrometry after reverse phase chromatography. Initial test reactions were performed using conditions described by Li et al. for Ile epimerization, except in $D_2O$ instead of $H_2O$. In our reaction, 0.05 mol % purified DsaD and DsaE (1:1) were combined in $D_2O$ with 50 mM sodium phosphate (pD 8.4), 0.1 mol % PLP and 1 mM Ile. Reagents were prepared in $D_2O$ to reduce 1H-water contamination to <1%. After an 8 h incubation with DsaD and DsaE at 37° C., a 1:1 mixture of $d_2$-2,3-L-Ile and $d_2$-2,3-L-allo-Ile was observed as the major product. No appreciable deuterium exchange (<3%) was observed in reactions without protein.

To begin probing the independent roles of the enzymes in this complex, we conducted H/D exchange reactions with just DsaD (excluding partner protein DsaE). We observed no transaminase activity under these conditions, in accordance with previous studies of the DsaD/E system, which would otherwise confound kinetic analysis.[29] However, L-Ile still appeared to bind DsaD, which catalyzed a single H/D exchange event.

Figure 2A:
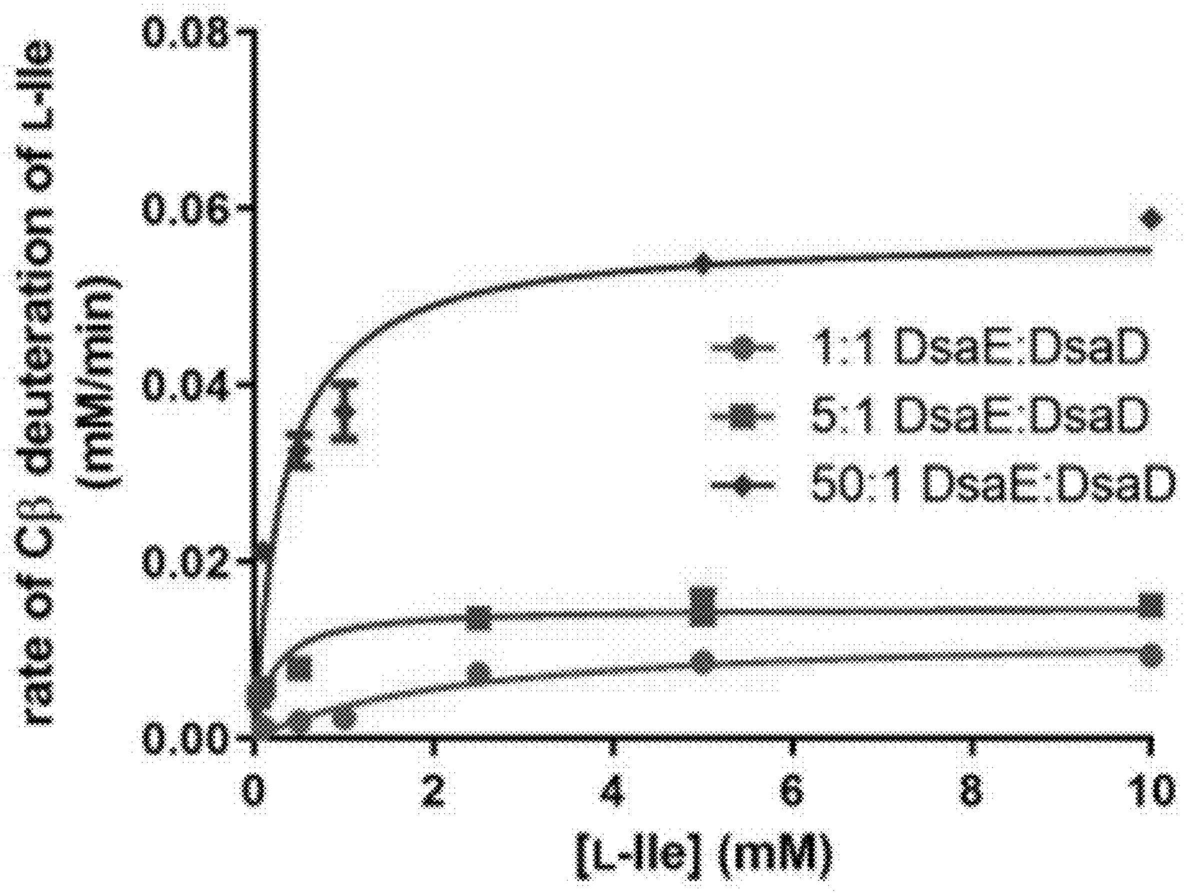
FIGS. 2A-2E. Steady-state kinetic analysis of H/D exchange by the Ile epimerization system.
Figure 2B:
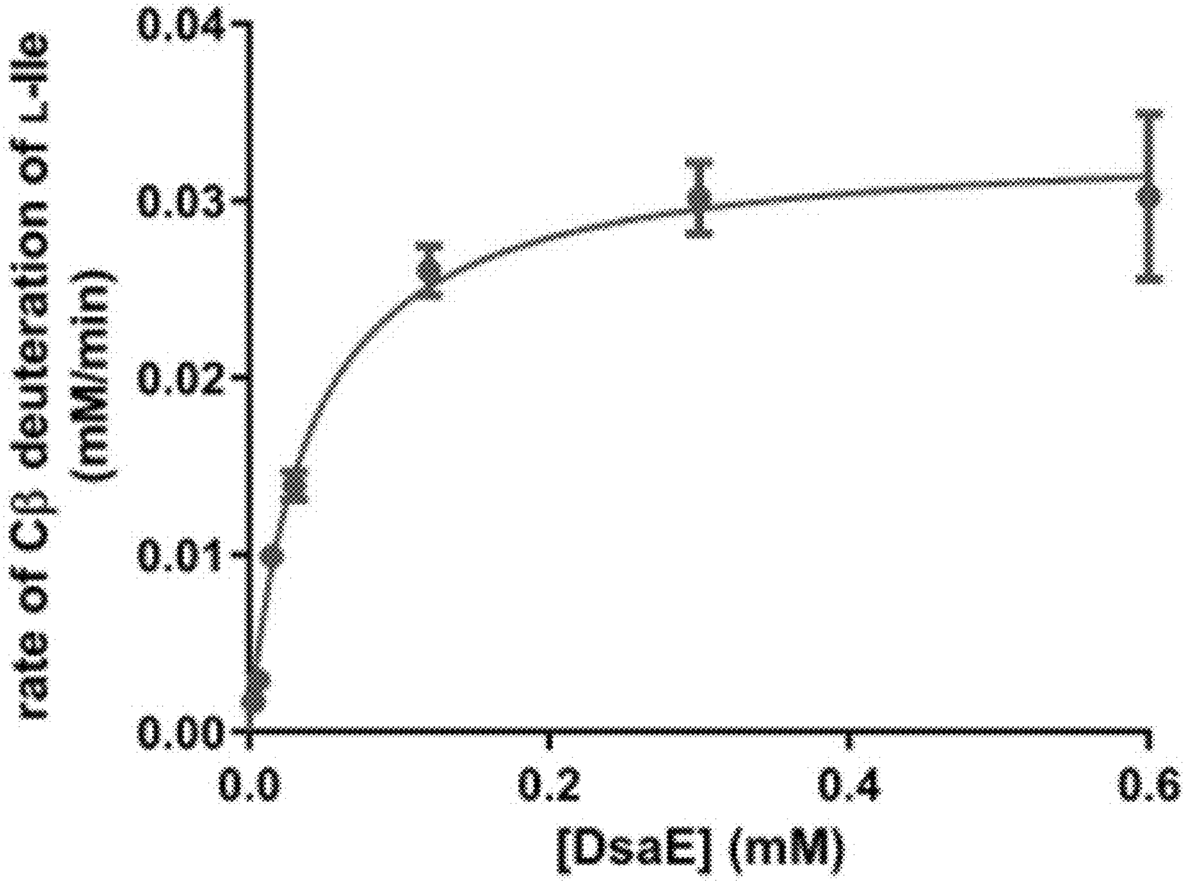
Figure 2C:
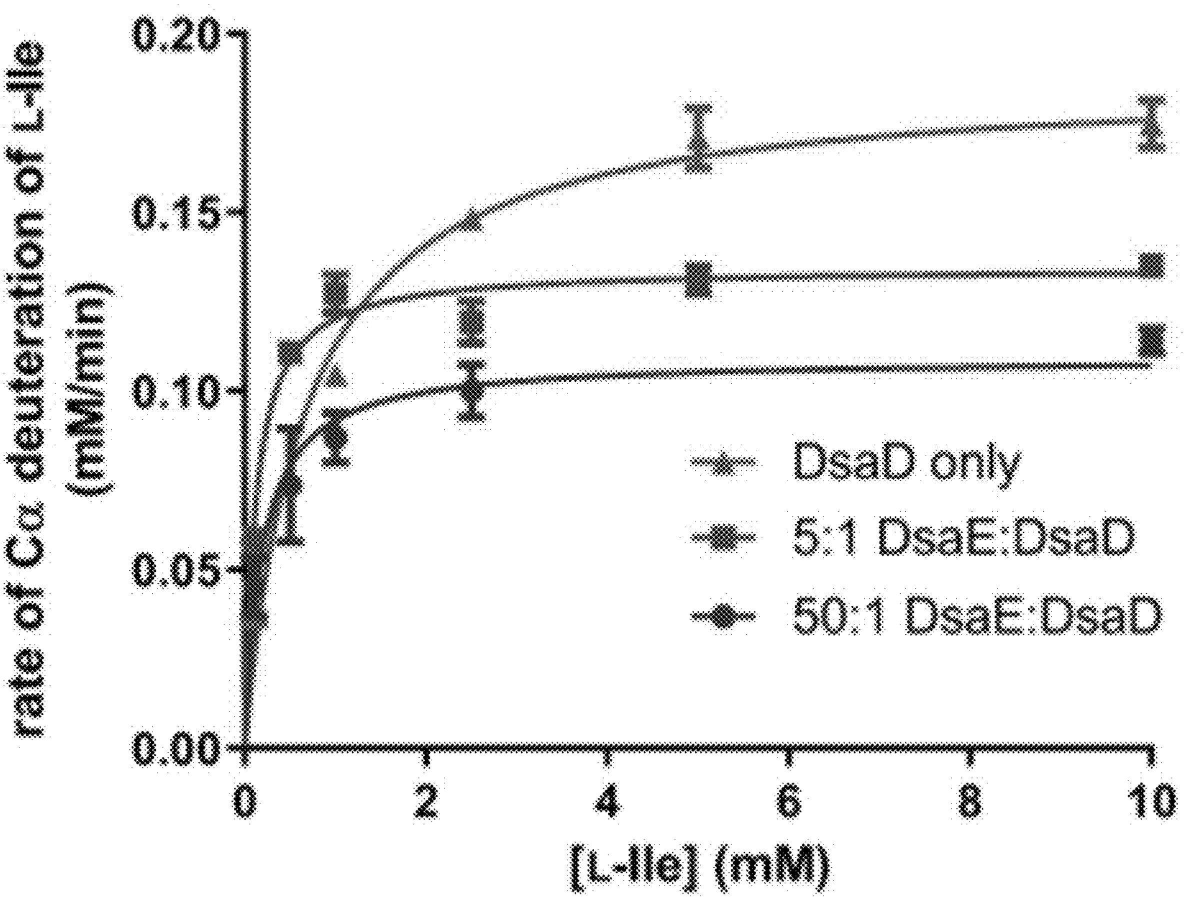
Figure 2D:
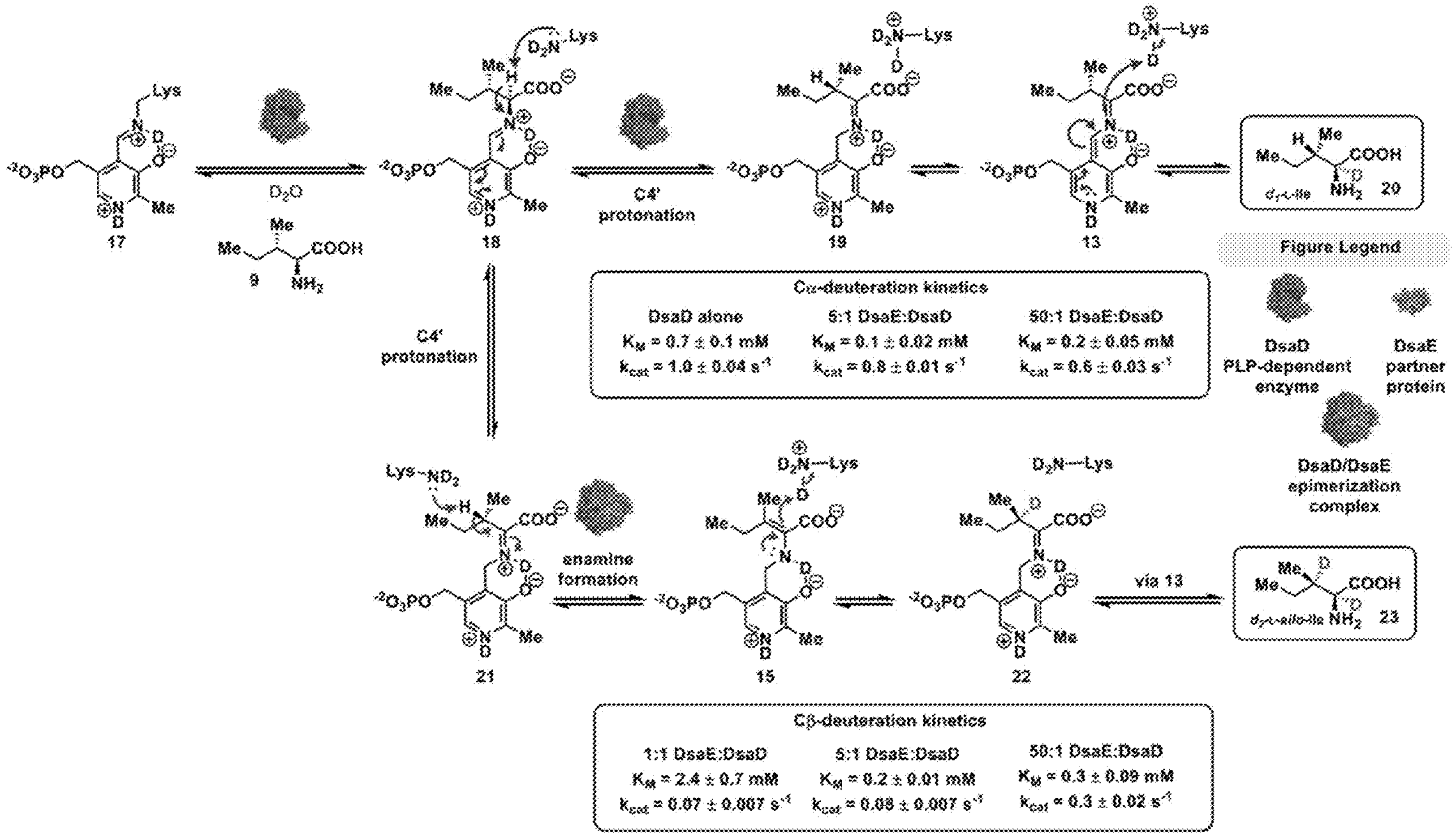

Steady-state kinetic analysis of H/D exchange reactions. With a reproducible assay in hand for the kinetic analysis of DsaD/E-catalyzed reactions, we sought to untangle the nature of the DsaD/E complex by assessing how changes in relative protein stoichiometry affect the activity. With one equivalent of partner protein DsaE, the Cβ-deuteration reaction proceeds with a $k_{cat}$ of 0.07±0.007 $s^{-1}$ and a $K_M$ value of 2.4±0.68 mM (FIGS. 2A and 2D). The addition of 5 equiv. of DsaE (5:1 DsaE:DsaD) did not significantly change $k_{cat}$, but we did observe an 11-fold decrease in the observed $K_M$, to 0.2±0.01 mM. Increasing partner protein stoichiometry further to 50 equiv. (50:1 DsaE:DsaD) led to a nearly 4-fold increase in $k_{cat}$ with a similar $K_M$ value (0.3±0.09 mM). To quantitate the strength of the DsaD/E interaction, we fixed the concentration of Ile and measured the initial rate of Cβ-deuteration. The reaction rate increased with additional equivalents of DsaE until reaching a plateau around 0.3 mM DsaE, corresponding to a 100:1 ratio of the two proteins (FIG. 2B). As the system is under the steady state, not equilibrium conditions, we fit these data to the Michaelis-Menten equation, from which we calculated a $K_M$ of 40±5 μM for the formation of the active DsaD/DsaE complex. This is a notably weak interaction when compared to other PLP-dependent enzymes that form protein complexes, such as the tryptophan synthases.[31,32] We next sought to probe how complexation affects the earlier steps in the reaction.

Figure 2E:
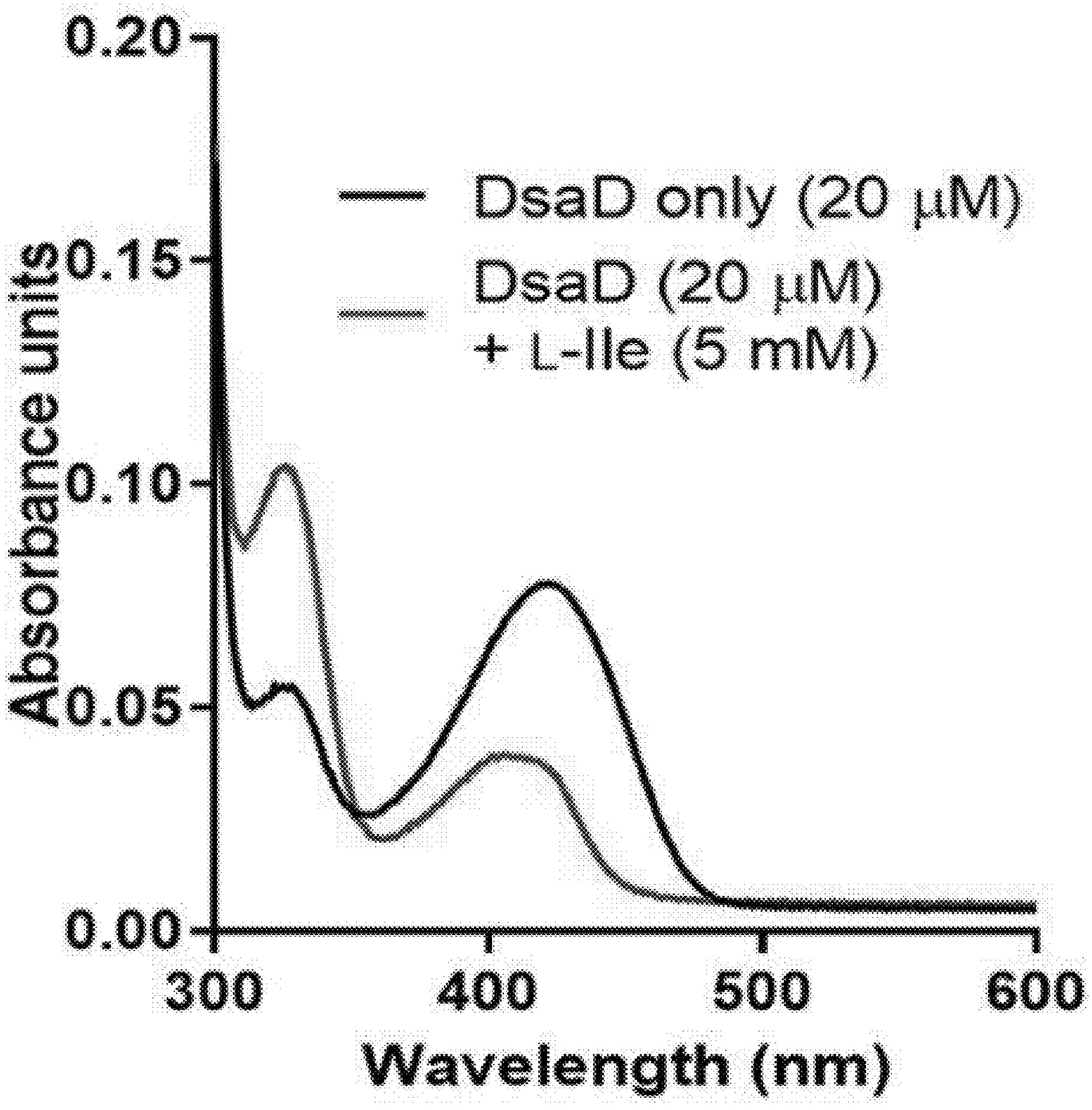

We measured the initial rates of Cα deuteration of Ile and fitting to the Michaelis-Menten equation (FIG. 2C), which showed that DsaD alone catalyzes Cα exchange with a $k_{cat}$ of 1.04±0.04 $s^{-1}$ and $K_M$ of 0.7±0.1 mM (FIG. 2D). Hence, the two reactions are not well-coupled, with Cα-exchange being much faster than the Cβ exchange reaction of the full complex under similar conditions. To assess how far into the mechanism DsaD can progress in the absence of DsaE, we performed a steady-state UV-visible spectroscopic analysis. In the absence of the substrate, DsaD exists as a classic internal aldimine (17) with a $\lambda_{max}$ of 423 nm (FIG. 2E) Upon the addition of saturating L-Ile, the internal aldmine peak disappears concomitant with the appearance of a new absorbance band at 328 nm, consistent with a ketimine adduct (21) with a protonated C4'.[33,34] Because DsaD has minimal BCAT activity, the iminium present in the ketimine adduct must be kinetically shielded from hydrolysis, which affords time for DsaE to bind and enable deprotonation at Cβ. We observed that DsaE binding lowers the apparent $K_M$ for Ile (0.12±0.02 mM) and, curiously, decreases the $k_{cat}$ of Cα-deuteration (0.75±0.01 $s^{-1}$). Further increasing the concentration of DsaE to 150 μM (50:1 DsaE:DsaD, above the $K_M$) did not significantly impact the observed $k_{cat}$ or $K_M$ for Cα-deuteration (FIG. 2D). Combined, these data indicate that Ile binds DsaD and forms a reversible ketimine adduct that can undergo multiple Cα exchange events. Upon DsaE binding, changes in the active site decrease the $K_M$ for Ile, slowing the rate of Cα deuteration, which we suggest increases the lifetime of bound Ile, providing time for the slower Cβ-epimerization reaction to occur.

Figure 3A:
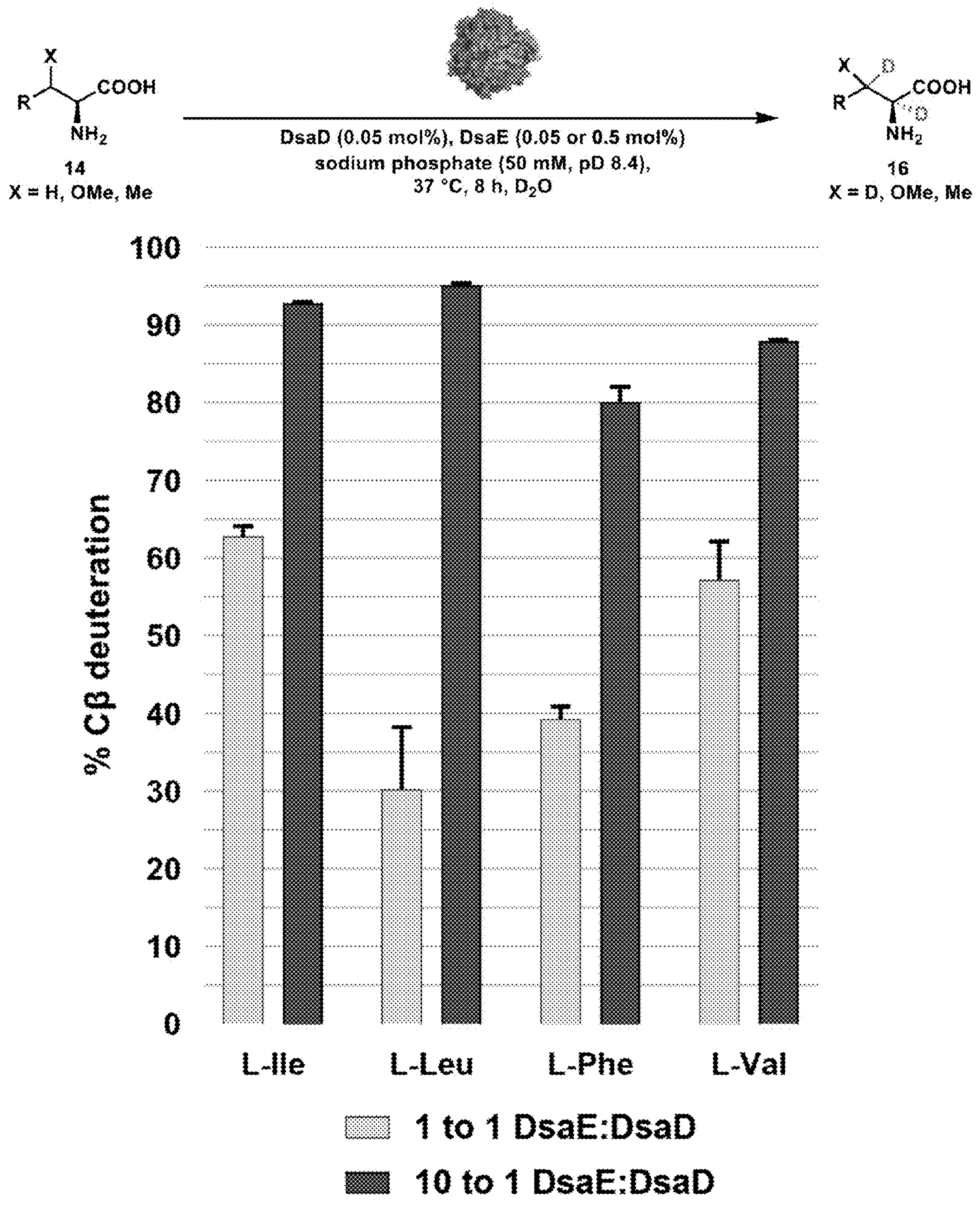
FIGS. 3A-3C. Optimization of H/D exchange reactions and evaluation of the substrate scope.
Figure 3B:
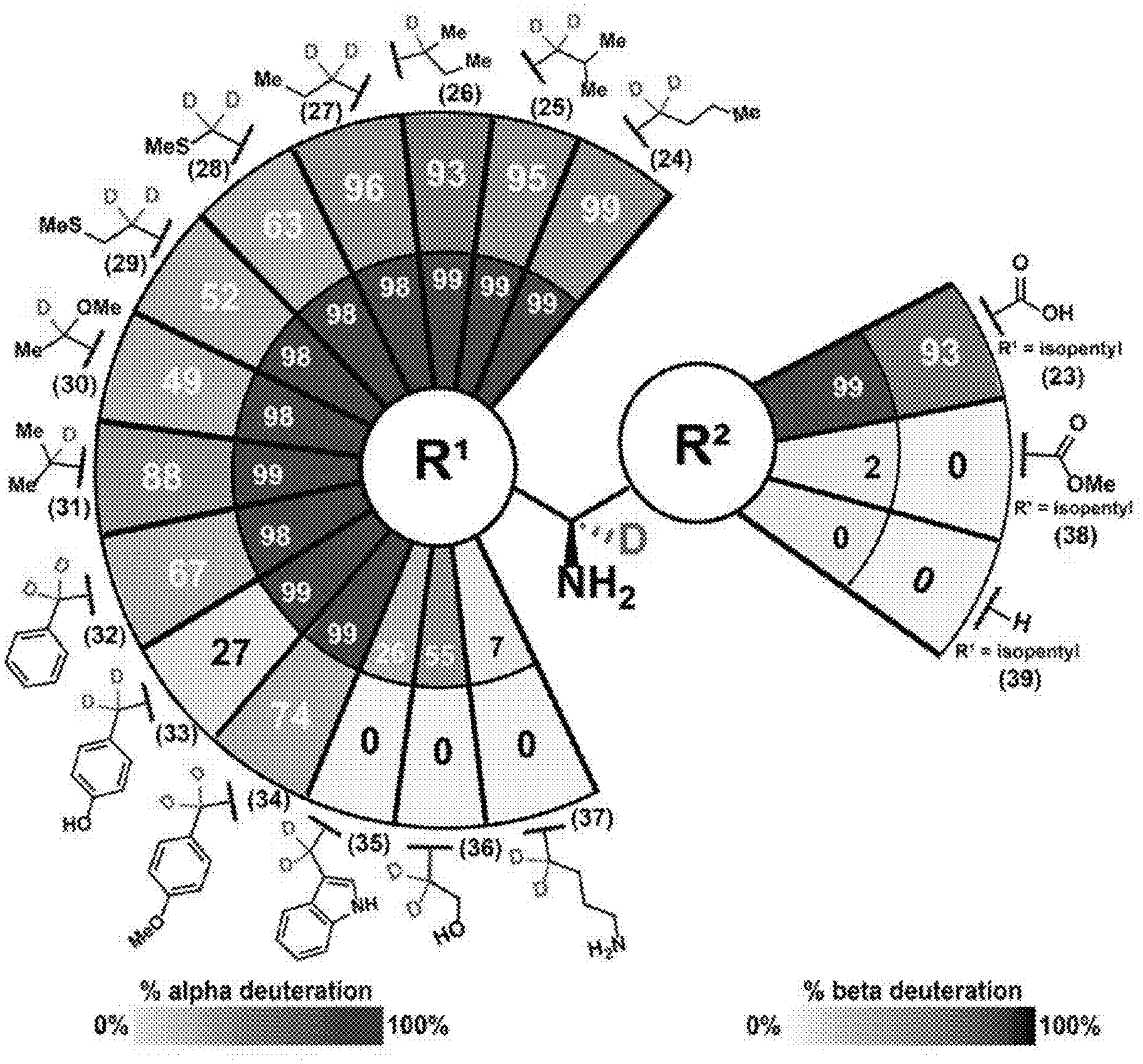

DsaD/E system catalyzes H/D exchange with a variety of amino acid substrates. Our analysis of the kinetic parameters of Cα and Cβ deuteration revealed core characteristics of the Ile epimerization system. However, it was still not known if the enzyme complex could productively engage amino acids other than Ile, as unbranched amino acids have no additional stereocenter to epimerize. To evaluate if the DsaD/E system could operate on other substrates, we subjected a small set of amino acids to Cα/β H/D exchange conditions (see FIG. 3A). We initially chose three amino acids that bear structural similarity to the native L-Ile: L-Leu, L-Val and L-Phe. Reaction conditions used a 1:1 mixture of DsaD and DsaE (both at 0.05 mol % catalyst). Interestingly, these reactions (FIG. 3A) delivered high conversion to the Cα-deuterated isotopologs (94-99% at Cα), showing that DsaD retains the ability to bind diverse substrates, similar to BCAT homologs.[35] We also observed the modest incorporation of deuterium at the Cβ-position (30-62% at Cβ), indicating that the Cβ-exchange reaction promoted by DsaE is robust to modest changes in the substrate structure (FIG. 3A). Although successful deuteration of non-native substrates suggests the possibility of a biocatalytic platform for site-selective deuteration of amino acids, the deuterium incorporation at Cβ would need to be increased to produce a practical system for scalable amino acid labeling.

The kinetic characterization of DsaD/E-catalyzed deuteration of Ile suggested that maximal rates of Cβ-deuteration could be achieved by increasing the concentration of the partner protein DsaE (FIG. 2B). We therefore increased the concentration of DsaE to 50 μM (10:1 DsaE:DsaD), which we hypothesized would bring the degree of labeling up to a synthetically useful level while keeping the overall catalyst loading within a reasonable range. Satisfyingly, a 10-fold increase (to 0.5 mol %) in DsaE loading improved Cβ-deuteration for the amino acids tested, delivering moderate to high levels of Cβ-exchange (FIG. 3A, 80-94%). With these conditions in hand, we sought to perform a more thorough evaluation of the substrate scope of Cα/Cβ-deuteration using the DsaD/E system.

We performed analytical scale Cα/Cβ deuteration reactions on a variety of standard and non-standard amino acids (FIG. 3B, 23-39). Reactions were performed in duplicate under the optimized conditions for deuteration of Ile (0.05 mol % DsaD and 0.5 mol % DsaE). Aliphatic amino acids underwent successful H/D exchange, showing high Cα and Cβ D-incorporation (88-99%) for Nle (24), Leu (25), Ile (26), Nva (27), and Val (31). Thioether-containing amino acids, such as S-Me-Cys (28) and Met (29), demonstrated high levels of exchange at Cα, but moderate levels of D-incorporation at Cβ. Aromatic amino acid Phe (32) showed high Cα deuteration, but moderate deuterium incorporation at Cβ (67%). In comparison, Tyr (33) underwent Cα-deuteration (99%), but low incorporation at Cβ (27%), presumably due to unfavorable interactions with the polar phenolic group. To test this hypothesis, we subjected the protected (OMe)-L-Tyr (34) to Cα/(3 deuteration conditions. To our delight, 34 underwent successful H/D exchange, with high D-incorporation at Cα (99%) and improved conversion at Cβ (74%). Interestingly, Trp (35) underwent Cα-deuteration, but no Cβ-deuteration. We observe a similar pattern with alcohol (homoserine, 36) and amine-containing (Lys, 37) substrates. Amino acids with hydroxyl moieties at Cβ (such as Thr and Ser) did not undergo any deuteration. However, protection of Thr as the methyl ether (30) enabled productive catalysis with the DsaD/E complex, with high levels of deuteration observed at Cα and moderate deuterium incorporation and scrambling of configuration at Cβ. These results indicate that DsaD is able to engage polar substrates, albeit with diminished efficiency, but that Cβ-deprotonation is not achieved unless the substrate is modified to reduce polar interactions.

Figure 3C:
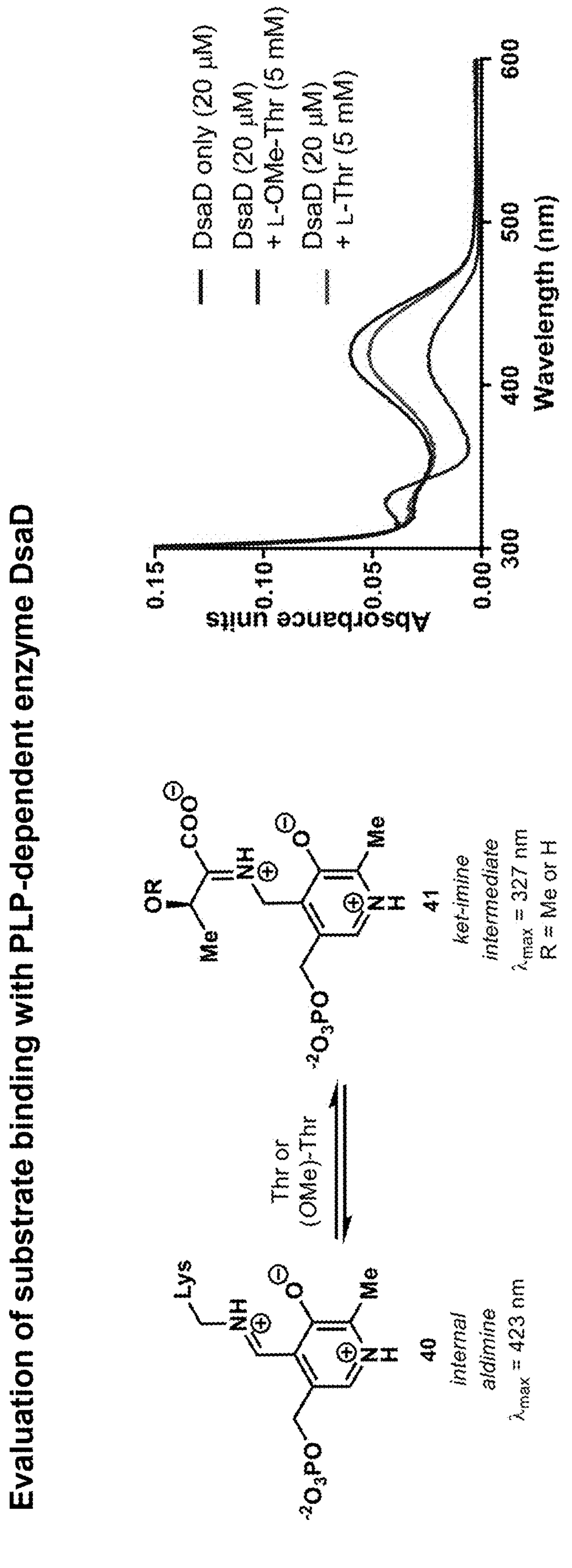

To assess whether catalysis with polar molecules is diminished because substrates cannot bind DsaD, or if the subsequent catalysis by the DsaD/E complex is perturbed, we leveraged steady-state UV-vis spectroscopy to monitor amino acid binding to DsaD. Following incubation of DsaD with unmodified Thr, no binding was observed, consistent with the results of the deuteration reaction screen (FIG. 3C). However, incubation of DsaD with the Thr methyl ether (L-(OMe)-Thr, 30) enables productive binding of this substrate and formation of the ketimine-species (41) (FIG. 3C). Based on these results, we conclude that the inability of DsaD to bind unprotected Cβ-hydroxy amino acids prevents productive catalysis by the Ile epimerization complex. This behavior is consistent with the preference for non-polar amino acids exhibited by related BCATs.[34] Notably, capping the polar group as an ether restores both DsaD binding and deuteration activity. Finally, we tested substrates lacking the α-carboxylate moiety, including the methyl ester of Ile (38) and isopentylamine (39). Neither of these substrates underwent deuteration by the DsaD/E system, demonstrating the importance of an α-carboxylate motif for achieving a catalytically productive pose in the active site.

In the original report by Li et al. describing DsaE, a homologous enzyme with 42% sequence identity, MfnH, was disclosed.[29] This homolog could operate with DsaD to catalyze Cβ-epimerization of Ile. Here, we test the ability of MfnH to productively catalyze H/D exchange reactions. We performed reactions with purified MfnH, DsaD (1:10 DsaD: MfnH), and L-Leu under the conditions described for DsaD/E-catalyzed reactions (FIG. 4). We found that L-Leu underwent efficient exchange at Cα (93%) and moderate deuterium labeling at Cβ (58%). Although the extent of deuteration using the DsaD-MfnH protein pair is diminished when compared to the native DsaD-DsaE pair under the same conditions, these experiments demonstrate the unique ability of these partner proteins to react with enzymes from outside their biosynthetic pathway. We also attempted isolation of MfnO, the native BCAT partner of MfnH, but produced only apo-enzyme.

Overall, the substrate screen used here showcases the broad tolerance of the DsaD/E system to changes in the side-chain structure, which would be challenging to assess without a robust assay to differentiate these distinct reactivities. Given the broad utility of deuterated amino acids, we envisioned that this unique dual protein system could be leveraged for preparative-scale synthesis.

Ile epimerization system catalyzes site- and enantioselective deuteration of amino acids. The reactions on the analytical scale demonstrated that the DsaD/DsaE catalytic system could achieve productive catalysis with a variety of amino acids. However, the development of a scalable biocatalytic method requires overcoming additional challenges. Operational simplicity is critical and demands facile access to the biocatalysts, particularly as high enzyme loadings for DsaE were required to achieve satisfactory H/D exchange at the Cβ-position. The use of clarified cell lysates would obviate costly protein purification and enable mmol-scale exchange reactions. Initial test reactions with L-Leu were carried out using lysates at an equivalent concentration of 1.2 mg wet cell mass/mL reaction for each biocatalyst. Because DsaE expresses similarly to DsaD, but has a lower molecular weight, these conditions provide a modest stoichiometric excess of the partner protein. These conditions limit the overall concentration of $^1$H-water in reactions to 5%, setting the maximum achievable D-incorporation to 95%. After 16 h, reactions were quenched and purified by reverse-phase chromatography. $^1$H NMR analysis (see FIG. 5) confirmed the production of the Cα and Cβ-deuterated isotopolog, L-Leu-2,3,3-$d_3$ (25) with high deuterium incorporation levels (95% for Cα and 86% for Cβ). UPLC analysis of isolated material following treatment of product with Marfey's reagent showed that stereoconfiguration at the Cα-position was retained under the reaction conditions (>99% ee), demonstrating that DsaD catalyzed an enantioselective H/D exchange. The level of D-incorporation in this system can also be controlled by modifying the concentration of 1H-water in the reaction. To increase labeling, we pre-dialyzed DsaD and DsaE lysates into a $D_2O$—$Na_3PO_4$ buffer (pD 8.4) for 2 h, then ran the H/D exchange reaction. Following this simple procedure, a reaction of L-Leu with dialyzed DsaD/E lysates (FIG. 6) led to very high D-incorporation at Cα (>99%) and Cβ (98%), demonstrating that nearly quantitative labeling can be achieved.

Figure 5:
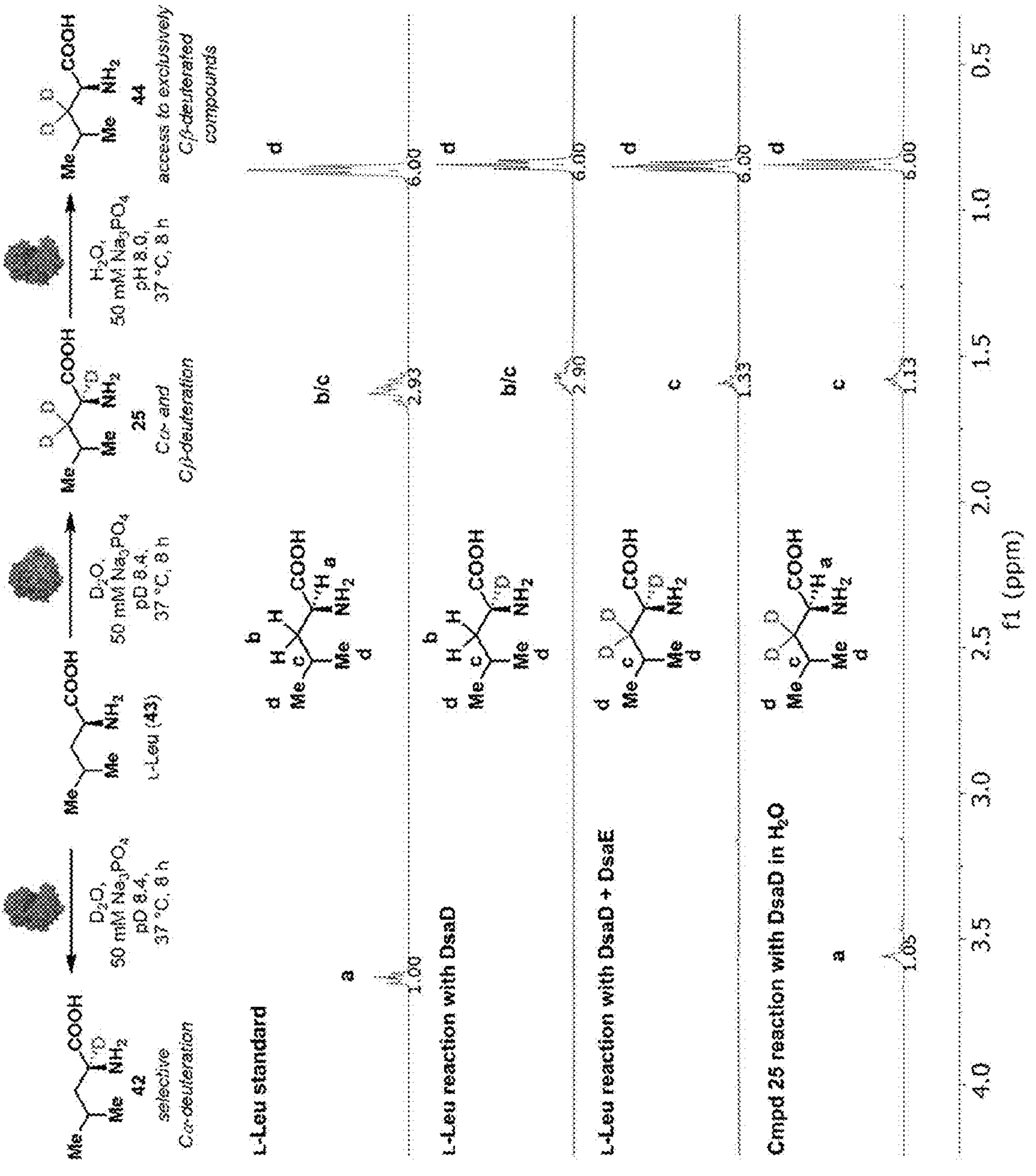
FIG. 5. $^1$H NMR analysis of site-selective deuteration of L-Leu. Reaction conditions: 20 mM L-Leu 2.5% v/v DsaD clarified lysate, 2.5% v/v DsaE clarified lysate (when needed), 50 mM sodium phosphate (pD 8.4), 0.1 mM PLP, $D_2O$ (99.9% D).
Figure 6:
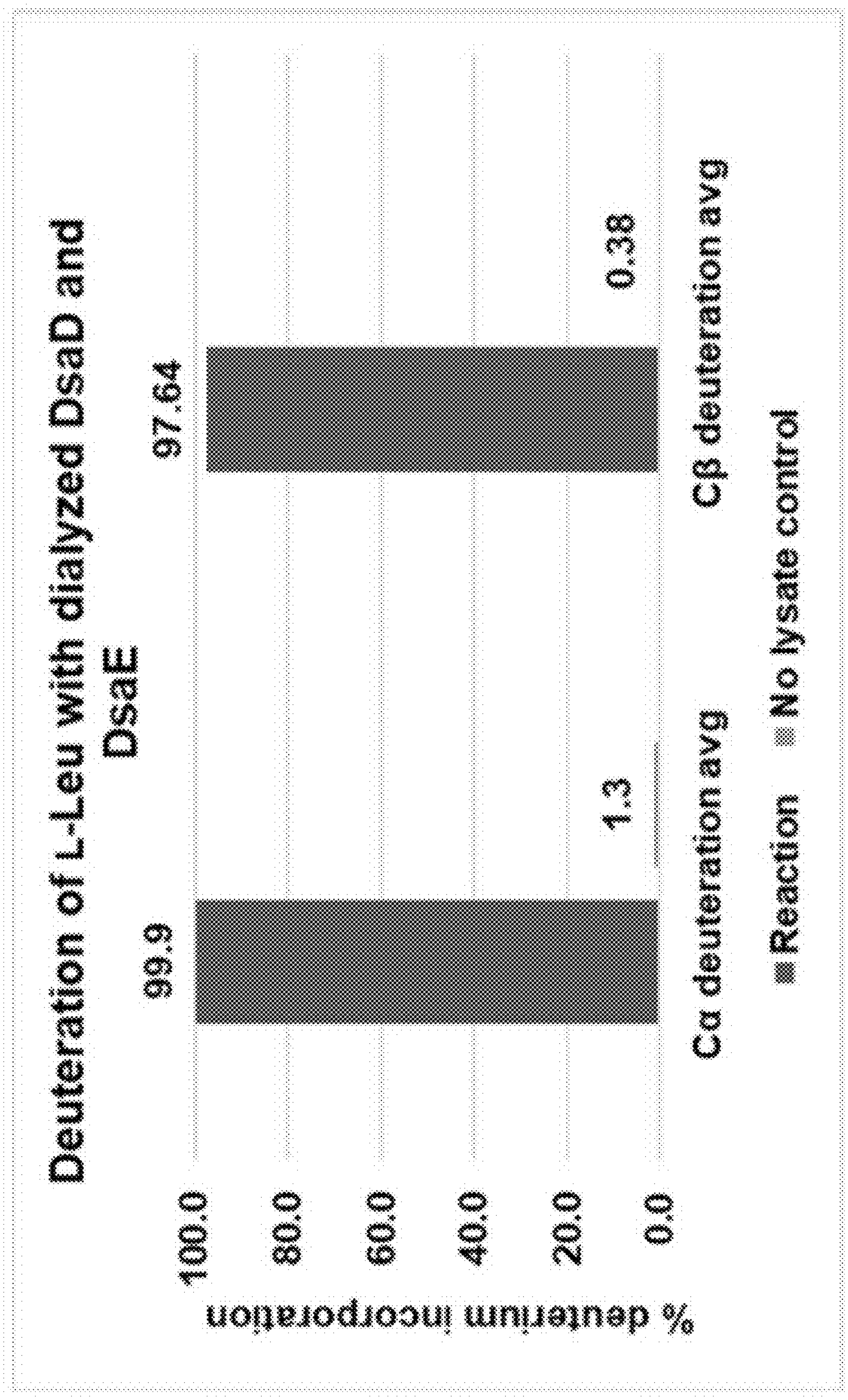
FIG. 6. Deuteration of L-Leu under conditions with minimal $H_2O$ contamination (99.9% D) using DsaD and DsaE lysates that were pre-dialyzed in 50 mM $D_2O$—$Na_3PO_4$ (pD 8.4). Reactions performed using the described procedure for analytical-scale H/D exchange. Results are reported as the average of 3 trials.

Inspired by the potential utility of the clarified cell lysate system to achieve site-selective deuteration, we envisioned that the addition of DsaD alone would catalyze scalable, selective H/D exchange at the Cα-position, including back-exchange of L-Leu-2,3,3-$d_3$ (25) to access L-Leu-3,3-$d_2$ (FIG. 5, 44). We treated L-Leu with DsaD in $D_2O$, leading to the site- and enantio-selective formation of Cα-deuterated L-Leu-2-d (42, 95% D incorporation, >99% ee), as determined by $^1$H NMR and UPLC analyses (FIG. 5). To further expand the scope of selective deuteration accessible using the DsaD/E system, we performed a two-step biocatalytic reaction sequence to access Cβ-deuterated products.

An initial reaction was performed with DsaD and DsaE to produce Cα,Cβ-deuterated L-Leu-2,3,3-$d_3$ (25). Following reaction quenching with acetone, centrifugation to remove protein products, and removal of acetone and $D_2O$ via rotary evaporation, the dry crude product mixture was subjected to standard reaction conditions with DsaD in water. This reaction led to washout of the Cα deuterium, providing exclusively Cβ-deuterated L-Leu-3,3-$d_2$ (44) with high levels of deuterium incorporation at Cβ (FIG. 5, 86% D incorporation and 98% ee). The site of H/D exchange in these reactions is dictated by the presence or absence of DsaE from the reaction conditions, enabling control of amino acid deuteration patterns.

Achieving site-selective Cα and Cβ deuteration in biocatalytic H/D exchange systems was an outstanding challenge, as enzymes that catalyze Cβ-exchange (such as PLP-dependent γ-synthases and γ-lyases) initially proceed through Cα-deprotonation, leading to concomitant H/D exchange at Cα. Therefore, catalyst-controlled site-selectivity provides a novel route by which the desired deuteration pattern can be achieved. The clarified cell lysate system used here serves as an efficient and inexpensive method for preparing the H/D exchange biocatalyst. For example, in an average 0.5 L expression of DsaE in *E. coli,* ~16 grams of cells are isolated, providing enough cell lysates from a single protein expression to perform H/D exchange on ~37 grams of L-Leu under the standard conditions developed here.

Because DsaE has been observed to operate with a variety of BCAT enzymes, we questioned whether DsaE, in just the presence of *E. coli* BCATs, could effect a Cα/Cβ-exchange without DsaD. We performed an analytical scale H/D exchange reaction on L-Leu (43) using 5% v/v DsaE lysate (FIG. 7). This reaction resulted in high labeling at Cα (>95%) and moderate deuterium incorporation at Cβ (70%), demonstrating that DsaE can utilize native BCATs present at biological concentrations (without overexpression) to perform H/D exchange.

Figure 8:
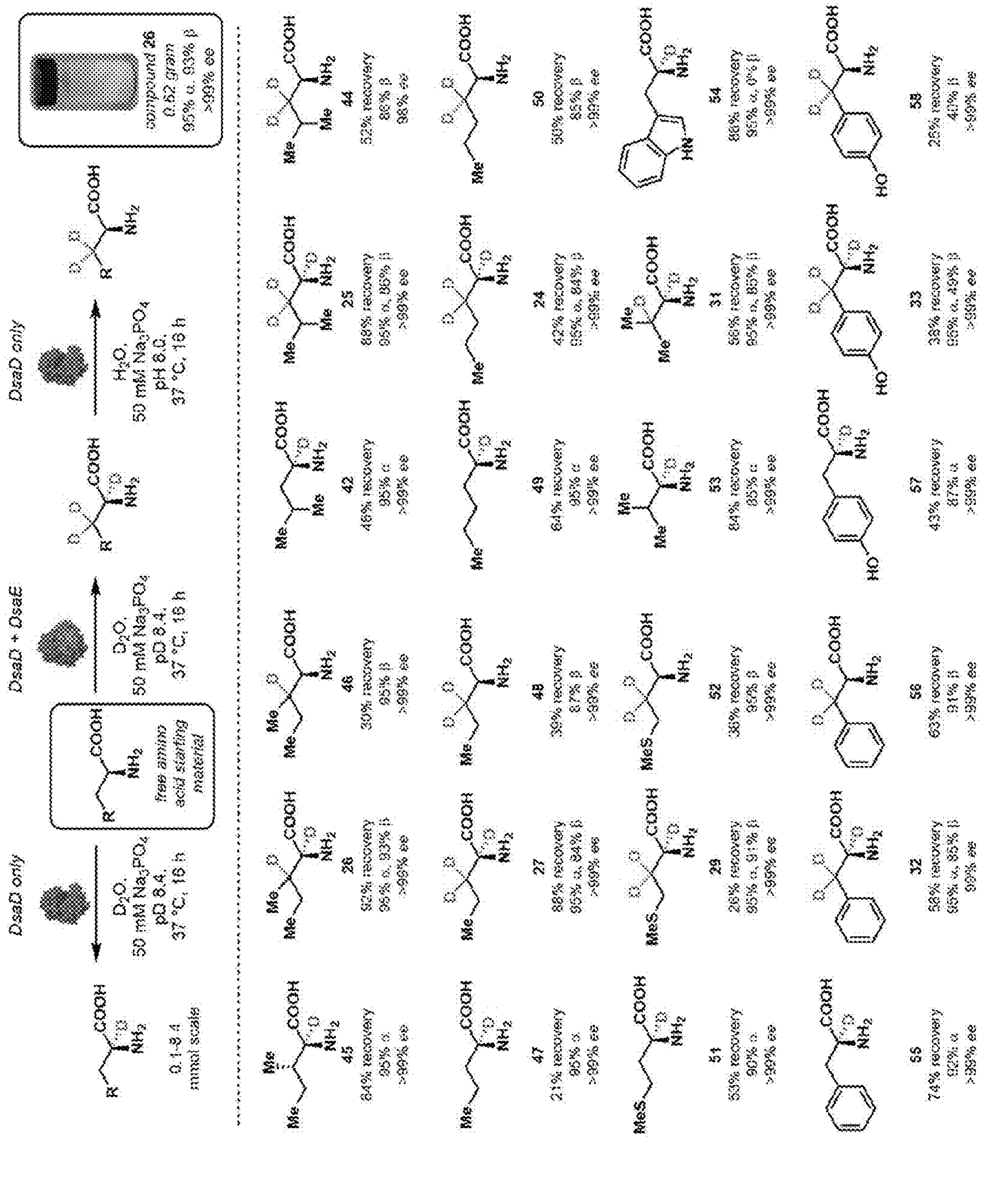
FIG. 8. Preparative-scale and site-selective deuteration of amino acids. Conditions: 10-20 mM amino acid, 2.5% v/v DsaD clarified lysate, 2.5% v/v DsaE clarified lysate, 50 mM sodium phosphate (pD 8.4), 0.1 mM PLP, $D_2O$ (99.9%).

After demonstrating the site- and enantioselectivity provided by the DsaD/E system on a single substrate, we pursued the scalable, site-selective deuteration of a variety of aliphatic and aromatic amino acids. We subjected both standard and non-standard amino acids to preparative scale deuteration conditions. Deuterium incorporation levels were determined by UPLC-MS analysis, and site-selectivity was confirmed by $^1$H NMR. In reactions with only DsaD, both aliphatic and aromatic amino acids (FIG. 8) demonstrated high deuterium incorporation at Cα (85-95%), with excellent retention of configuration (>99% ee). We also performed 0.2-0.5 mmol scale reactions with DsaD and DsaE to catalyze H/D exchange at both Cα and Cβ. Aliphatic amino acids were successfully deuterated, with high incorporation levels at Cα (95%) and Cβ (84-93%) and >99% ee. As a further demonstration of scalability, Ile was deuterated on >600 mg scale, delivering high levels of deuteration at Cα (95%) and Cβ (93%). Aromatic and thioether-containing amino acids proved slightly more challenging and reactions were run at a lower substrate loading (10 mM) to produce higher deuterium incorporation levels. Under these conditions, L-Phe-2,3,3-$d_3$ (32) was produced with high deuterium incorporation at Cα (95%) and Cβ (85%). However, the Cβ-deuteration of L-Tyr was less efficient, leading to moderate Cβ deuterium incorporation (49%). Cα deuterium incorporation was still high for this reaction (95%), suggesting that the catalytic limitations of the DsaD/E complex are different than observed with DsaD as a standalone enzyme. These observations are in agreement with analytical scale experiments, which showed that unprotected polar functional groups led to poor incorporation of deuterium at Cβ. We also note that clarified cell lysate reactions led to improved deuterium incorporation with poor substrates when compared to purified enzyme reactions. This improvement is likely due to relatively high protein titers in clarified lysates and demonstrates that lysate-based approaches can contend with the use of costly purified enzymes.

As there are limited site-selective methods for accessing Cβ-deuterated amino acids, we last sought to demonstrate the utility of the DsaD/E enzymatic platform for accessing this challenging pattern of isotope labeling. We performed Cα/Cβ deuteration on a panel of amino acids, quenched the reactions and resubjected the crude product to Cα deuterium washout with DsaD in $H_2O$. Following this sequence, aliphatic amino acids were labeled with high deuterium incorporation at Cβ (84%-95%) and excellent retention of configuration (98-99% ee). Reactions with aromatic and thioether-containing amino acids were again performed at lower substrate loading (10 mM), leading to high deuterium incorporation at Cβ for L-Phe (91%) and moderate incorporation for L-Tyr (40%). We note that even incomplete deuteration can provide useful material, as mixtures of isotopologs can be deployed for powerful mechanistic experiments, such as isotopic labeling and elucidation of kinetic isotope effects.[2,5]

The relatively wide scope of this native enzyme system, along with its slow rate of reaction, contrasts with other PLP-dependent enzymes. Because L-allo-Ile is only required in small amounts for secondary metabolism, and L-Ile is essential for protein synthesis, there is a clear selective pressure for this complex to only operate at a slow rate. In contrast, in the absence of $D_2O$, the activity of the DsaD/E complex is totally masked for substrates lacking a Cβ-branch. Consequently, there is no selective pressure for the system to discriminate against any standard amino acid other than Thr. Our data here show that this selectivity is achieved on the simple basis of hydrophobicity, which leaves open the wide chemical space that reacts in the H/D-exchange disclosed here.

CONCLUSIONS

We have characterized the two protein-dependent Ile epimerization system and demonstrated the synthetic utility of this system for the scalable and selective deuteration of several α-amino acids. H/D exchange was initially used as a convenient proxy for epimerase activity. Kinetic experiments illustrated that rates of Cβ-deuteration are highly dependent on the concentration of partner protein, DsaE, with a comparatively weak $K_M$ for their association, 40 uM. These observations were used to improve Cα and Cβ deuterium incorporation in analytical experiments. Substrate screening efforts identified numerous amino acids that could undergo productive H/D exchange reactions, including a variety of aliphatic and aromatic amino acids. Furthermore, a preparative-scale biocatalytic reaction platform was established which enabled access to selectively deuterated materials with Cα, Cα/Cβ, and the challenging Cβ-only deuteration patterns. This operationally simple and inexpensive reaction system delivers the desired deuteration pattern without the need for protein purification or multi-step substrate deuteration procedures. These data provide a foundation for future study of the intriguing DsaD/E protein complex, as well as demonstrate that this system can be leveraged to efficiently access a variety of amino acid isotopologs.

REFERENCES CITED

The following references are incorporated herein by reference:

(1) Krumbiegel, P. Large Deuterium Isotope Effects and Their Use: A Historical Review. *Isotopes Environ. Health Stud.* 2011, 47 (1), 1-17.

(2) Atzrodt, J.; Derdau, V.; Kerr, W. J.; Reid, M. Deuterium- and Tritium-Labelled Compounds: Applications in the Life Sciences. *Angew. Chemie—Int. Ed.* 2018, 57 (7), 1758-1784.

(3) Pirali, T.; Serafini, M.; Cargnin, S.; Genazzani, A. A. Applications of Deuterium in Medicinal Chemistry. *J. Med. Chem.* 2019, 62 (11), 5276-5297.

(4) Gant, T. G. Using Deuterium in Drug Discovery: Leaving the Label in the Drug. *J. Med. Chem.* 2014, 57 (9), 3595-3611.

(5) Nelson, S. D.; Trager, W. F. The Use of Deuterium Isotope Effects to Probe the Active Site Properties, Mechanism of Cytochrome P450-Catalyzed Reactions, and Mechanisms of Metabolically Dependent Toxicity. *Drug Metab. Dispos.* 2003, 31 (12), 1481-1498.

(6) Hanashima, S.; Ibata, Y.; Watanabe, H.; Yasuda, T.; Tsuchikawa, H.; Murata, M. Side-Chain Deuterated Cholesterol as a Molecular Probe to Determine Membrane Order and Cholesterol Partitioning. *Org. Biomol. Chem.* 2019, 17 (37), 8601-8610.

(7) Thielges, M. C.; Case, D. A.; Romesberg, F. E. Carbon-Deuterium Bonds as Probes of Dihydrofolate Reductase. *J. Am. Chem. Soc.* 2008, 130 (20), 6597-6603.

(8) Sheppard, D.; Li, D. W.; Brüschweiler, R.; Tugarinov, V. Deuterium Spin Probes of Backbone Order in Proteins: 2H NMR Relaxation Study of Deuterated Carbon a Sites. *J. Am. Chem. Soc.* 2009, 131 (43), 15853-15865.

(9) Kelly, N. M.; Sutherland, A.; Willis, C. L. Syntheses of Amino Acids Incorporating Stable Isotopes. *Nat. Prod. Rep.* 1997, 14 (3), 205-220.

(10) Voges, R. From Chiral Bromo [$^{13,\ 14}C_n$] Acetyl Sultams to Complex Molecules Singly/Multiply Labelled with Isotopic Carbon. 2002, No. February, 867-897.

(11) Grocholska, P.; Bachor, R. Trends in the Hydrogen-Deuterium Exchange at the Carbon Centers. Preparation of Internal Standards for Quantitative Analysis by LC-MS. *Molecules* 2021, 26, 2989-3014.

(12) Kirby, G. W.; Michael, J. Labelling of Aromatic Amino-Acids Stereoselectively with Tritium in the β-Methylene Group: The Stereochemistry of Hydroxylation in the Biosynthesis of Haemanthamine. *J. Chem. Soc. D Chem. Commun.* 1971, No. 4, 187-188.
(13) Maegawa, T.; Akashi, A.; Esaki, H.; Aoki, F.; Sajiki, H.; Hirota, K. Efficient and Selective Deuteration of Phenylalanine Derivatives Catalyzed by Pd/C. *Synlett* 2005, No. 5, 845-847.
(14) Easton, C. J.; Hutton, C. A. Synthesis of Each Stereoisomer of [3-$^2H_1$] Phenylalanine and Evaluation of the Stereochemical Course of the Reaction of (R)-Phenylalanine with (S)-Phenylalanine Ammonia-Lyase. *J. Chem. Soc. Perkin Trans.* 1 1994, 3545-3548.
(15) Nukuna, B. N.; Goshe, M. B.; Anderson, V. E. Sites of Hydroxyl Radical Reaction with Amino Acids Identified by 2H NMR Detection of Induced 1H/2H Exchange. *J. Am. Chem. Soc.* 2001, 123 (6), 1208-1214.
(16) Thompson, C. M.; McDonald, A. D.; Yang, H.; Cavagnero, S.; Buller, A. R. Modular Control of L-Tryptophan Isotopic Substitution via an Efficient Biosynthetic Cascade. *Org. Biomol. Chem.* 2020, 18 (22), 4189-4192.
(17) Pająk, M.; Pałka, K.; Winnicka, E.; Kańska, M. The Chemo-Enzymatic Synthesis of Labeled 1-Amino Acids and Some of Their Derivatives. *J. Radioanal. Nucl. Chem.* 2018, 317 (2), 643-666.
(18) Wong, C. H.; Whitesides, G. M. Enzyme-Catalyzed Organic Synthesis: Regeneration of Deuterated Nicotinamide Cofactors for Use in Large-Scale Enzymatic Synthesis of Deuterated Substances. *J. Am. Chem. Soc.* 1983, 105 (15), 5012-5014.
(19) Rowbotham, J. S.; Ramirez, M. A.; Lenz, O.; Reeve, H. A.; Vincent, K. A. Bringing Biocatalytic Deuteration into the Toolbox of Asymmetric Isotopic Labelling Techniques. *Nat. Commun.* 2020, 11 (1), 1-7.
(20) Chanatry, J. A.; Schafer, P. H.; Kim, M. S.; LeMaster, D. M. Synthesis of α,β-Deuterated 15N Amino Acids Using a Coupled Glutamate Dehydrogenase-Branched-Chain Amino Acid Aminotransferase System. *Anal. Biochem.* 1993, 213, 147-151.
(21) Chun, S. W.; Narayan, A. R. H. Biocatalytic, Stereoselective Deuteration of α-Amino Acids and Methyl Esters. *ACS Catal.* 2020, 10 (13), 7413-7418.
(22) Long, G. J.; Whelan, B. D. J. Enzymatic Transamination: The Synthesis of α,β,β-Trideutero-L-Glutamic Acid and α-Deutero-L-Glutamic Acid. *Aust. J. Chem.* 1969, 22, 1779-1782.
(23) Golichowski, A.; Harruff, R. C.; Jenkins, W. T. The Effects of pH on the Rates of Isotope Exchange Catalyzed by Alanine Aminotransferase. *Arch. Biochem. Biophys.* 1977, 178, 459-467.
(24) Homer, R. J.; Kim, M. S.; LeMaster, D. M. The Use of Cystathionine Gamma-Synthase in the Production of Alpha and Chiral Beta Deuterated Amino Acids. *Analytical Biochemistry.* 1993, pp 211-215.
(25) Esaki, N.; Sawada, S.; Tanaka, H.; Soda, K. Enzymatic Preparation of Alpha- and Beta-Deuterated or Tritiated Amino Acids with L-Methionine Gamma-Lyase. *Anal. Biochem.* 1982, 119, 281-285.
(26) Guggenheim, S.; Flavin, M. Cystathionine Gamma-Synthase. A Pyridoxal Phosphate Enzyme Catalyzing Rapid Exchanges of Beta and Alpha Hydrogen Atoms in Amino Acids. *J. Biol. Chem.* 1969, 244 (22), 6217-6227.
(27) Hadener, A.; Tamm, C. H. Synthesis of Specifically Labelled L-Phenylalanines Using Phenylalanine Ammonia Lyase Activity. *J. Label. Compd. Radiopharm.* 1987, 24 (11), 1291-1306.
(28) Hanson, K. R.; Wightman, R. H.; Staunton, J.; Battersby, A. R. Stereochemical Course of the Elimination Catalysed by L-Phenylalanine Ammonia-Lyase and the Configuration of 2-Benzamidocinnamic Azlactone. *J. Chem. Soc. D Chem. Commun.* 1971, No. 4, 185-186.
(29) Li, Q.; Qin, X.; Liu, J.; Gui, C.; Wang, B.; Li, J.; Ju, J. Deciphering the Biosynthetic Origin of 1-allo-Isoleucine. *J. Am. Chem. Soc.* 2016, 138 (1), 408-415.
(30) Bhushan, R.; Bruckner, H. Marfey's Reagent for Chiral Amino Acid Analysis: A Review. *Amino Acids* 2004, 27 (3-4), 231-247.
(31) Busch, F.; Rajendran, C.; Heyn, K.; Schlee, S.; Merkl, R.; Sterner, R. Ancestral Tryptophan Synthase Reveals Functional Sophistication of Primordial Enzyme Complexes. *Cell Chem. Biol.* 2016, 23 (6), 709-715.
(32) Buller, A. R.; Brinkmann-Chen, S.; Romney, D. K.; Herger, M.; Murciano-Calles, J.; Arnold, F. H. Directed Evolution of the Tryptophan Synthase β-Subunit for Stand-Alone Function Recapitulates Allosteric Activation. *Proc. Natl. Acad. Sci.* 2015, 112 (47), 14599-14604.
(33) Bersudnova, E. Y.; Boyko, K. M.; Popov, V. O. Properties of Bacterial and Archaeal Branched-Chain Amino Acid Aminotransferases. *Biochem.* 2017, 82 (13), 1572-1591.
(34) Hutson, S. Structure and Function of Branched Chain Aminotransferases. *Prog. Nucleic Acid Res. Mol. Biol.* 2001, 70, 175-206.
(35) Yvon, M.; Chambellon, E.; Bolotin, A.; Roudot-Algaron, F. Characterization and Role of the Branched-Chain Aminotransferase (BcaT) Isolated from *Lactococcus Lactis* Subsp. *cremoris* NCDO 763. *Appl. Environ. Microbiol.* 2000, 66 (2), 571-577.
(36) Lemaster, D. M. Deuterium Labelling in NMR Structural Analysis of Larger Proteins. *Q. Rev. Biophys.* 1990, 23, 133-174.
(37) Furuta, T.; Takahashi, H.; Kasuya, Y. Evidence for a Carbanion Intermediate in the Elimination of Ammonia from L-Histidine Catalyzed by Histidine Ammonia-Lyase. *J. Am. Chem. Soc.* 1990, 112, 3633-3636.

What is claimed is:

1. A method of making a deuterated amino acid, the method comprising contacting a non-deuterated amino acid having an α-position carbon atom and a β-position carbon atom with deuterium and a protein selected from the group consisting of a branched-chain aminotransferase and a combination of a branched-chain aminotransferase and a partner protein, for a time and at a temperature to selectively deuterate the non-deuterated amino acid at the α-position carbon atom to yield a Cα-deuterated amino acid or to selectively deuterate the non-deuterated amino acid at both the α-position and the β-position carbon atom to yield a Cα- and Cβ-deuterated amino acid, wherein the branched-chain aminotransferase is a protein comprising an amino acid sequence at least 85% identical to SEQ ID NO: 1, and wherein the partner protein is a protein comprising an amino acid sequence at least 85% identical to SEQ ID NO: 3 or SEQ ID NO: 4.

2. The method of claim 1, wherein:

the branched-chain aminotransferase is a protein comprising an amino acid sequence of at least 95% identical to SEQ ID NO: 1; and the partner protein is a protein comprising an amino acid sequence of at least 95% identical to SEQ ID NO: 3 or SEQ ID NO: 4.

3. The method of claim 1, wherein the non-deuterated amino acid is contacted with the deuterium and the branched-chain aminotransferase to yield a Cα-deuterated amino acid.

4. The method of claim 1, wherein the non-deuterated amino acid is contacted with the deuterium and the combination of the branched-chain aminotransferase and the partner protein to yield a Cα- and Cβ-deuterated amino acid.

5. The method of claim 1, further comprising contacting the Cα- and Cβ-deuterated amino acid with non-deuterium hydrogen and the branched-chain aminotransferase, for a time and at a temperature to selectively replace the deuterium at the α-position carbon atom with the non-deuterium hydrogen to yield a Cβ-deuterated amino acid.

6. The method of claim 5, wherein the non-deuterium hydrogen is provided as non-deuterated water.

7. The method of claim 1, wherein the deuterium is provided as deuterated water.

8. The method of claim 1, wherein the protein is cell-free protein.

9. The method of claim 1, wherein the temperature ranges from about 20° C. to about 40° C.

10. The method of claim 1, where in the time ranges from about 1 hour to about 24 hours.

11. A method of making a deuterated amino acid, the method comprising contacting a non-deuterated amino acid having an α-position carbon atom and a β-position carbon atom with deuterium and a combination of a branched-chain aminotransferase and a partner protein, for a time and at a temperature to selectively deuterate the non-deuterated amino acid at both the α-position and the β-position carbon atom to yield a Cα- and Cβ-deuterated amino acid, wherein the branched-chain aminotransferase is a protein comprising an amino acid sequence at least 85% identical to SEQ ID NO: 2, and wherein the partner protein is a protein comprising an amino acid sequence at least 85% identical to SEQ ID NO: 3 or SEQ ID NO: 4.

12. A method of making a deuterated amino acid, the method comprising contacting a non-deuterated amino acid having an α-position carbon atom and a β-position carbon atom with deuterium and a branched-chain aminotransferase, for a time and at a temperature to selectively deuterate the non-deuterated amino acid at the α-position carbon atom to yield a Cα-deuterated amino acid, wherein the branched-chain aminotransferase is a protein comprising an amino acid sequence at least 85% identical to SEQ ID NO: 1.

13. A method of making a deuterated amino acid, the method comprising:

contacting a non-deuterated amino acid having an α-position carbon atom and a β-position carbon atom with deuterium and a combination of a branched-chain aminotransferase and a partner protein, for a time and at a temperature to selectively deuterate the non-deuterated amino acid at both the α-position and the β-position carbon atom to yield a Cα- and Cβ-deuterated amino acid; and contacting the Cα- and Cβ-deuterated amino acid with non-deuterium hydrogen and the branched-chain aminotransferase, for a time and at a temperature to selectively replace the deuterium at the α-position carbon atom with the non-deuterium hydrogen to yield a Cβ-deuterated amino acid;

wherein the branched-chain aminotransferase is a protein comprising an amino acid sequence at least 85% identical to SEQ ID NO: 1; and wherein the partner protein is a protein comprising an amino acid sequence at least 85% identical to SEQ ID NO: 3 or SEQ ID NO: 4.

* * * * *

SEQUENCE LISTING

```
Sequence total quantity: 10
SEQ ID NO: 1            moltype = AA  length = 377
FEATURE                 Location/Qualifiers
source                  1..377
                        mol_type = protein
                        note = DsaD
                        organism = Streptomyces scopuliridis
SEQUENCE: 1
MHIVTTPVAR PLTAQERTER CAAPAFGTAF TEHMVSARWN PEQGWHDAEL VPYGPLLLDP  60
ATVGLHYGQV VFEGLKAFRS HTGEVAVFRP DAHAERMRAS ARRLMMPEPP EELFLAAVDA  120
LVAQDQEWIP DDPGMSLYLR PILFASERTL ALRPAREYRF LLVAFITEGY FGPAQRPVRV  180
```

-continued

```
WVTDEYSRAA AGGTGAAKCA GNYAGSLLAQ EEAQRKGCDQ VVWLDPVERN WVEEMGGMNL  240
FFVYEAGGSA RLVTPPLTGS LLPGVTRDAL LRLAPTLGVP VSEAPLSLEQ WRADCASGAI  300
TEVFACGTAA RISPVNEVST KDGSWTIGAG APAEGGVAAG EVTGRLSAAL FGIQRGELPD  360
SHSWMRPVSP ARQSAIT                                                 377

SEQ ID NO: 2            moltype = AA  length = 309
FEATURE                 Location/Qualifiers
source                  1..309
                        mol_type = protein
                        note = BCAT
                        organism = Escherichia coli
SEQUENCE: 2
MTTKKADYIW FNGEMVRWED AKVHVMSHAL HYGTSVFEGI RCYDSHKGPV VFRHREHMQR  60
LHDSAKIYRF PVSQSIDELM EACRDVIRKN NLTSAYIRPL IFVGDVGMGV NPPAGYSTDV  120
IIAAFPWGAY LGAEALEQGI DAMVSSWNRA APNTIPTAAK AGGNYLSSLL VGSEARRHGY  180
QEGIALDVNG YISEGAGENL FEVKDGVLFT PPFTSSALPG ITRDAIIKLA KELGIDVREQ  240
VLSRESLYLA DEVFMSGTAA EITPVRSVDG IQVGEGRCGP VTKRIQQAFF GLFTGETEDK  300
WGWLDQVNQ                                                          309

SEQ ID NO: 3            moltype = AA  length = 124
FEATURE                 Location/Qualifiers
source                  1..124
                        mol_type = protein
                        note = DsaE
                        organism = Streptomyces scopuliridis
SEQUENCE: 3
MTESSPTEVN EARVREYYRL VDADDVLGLV SLFAEDAVYR RPGYEPMRGH TGLTAFYTGE  60
RVIESGRHTV ATVVARGDQV AVNGVFEGVL KDGRQVRLEF ADFFLLNGER RFSRRDTYFF  120
APLV                                                               124

SEQ ID NO: 4            moltype = AA  length = 116
FEATURE                 Location/Qualifiers
source                  1..116
                        mol_type = protein
                        note = MfnH
                        organism = Streptomyces drozdowiczii
SEQUENCE: 4
MGRSETIRRY YELVDAADYE AMFRIFCDDL IYERAGTEPI EGIVEFRHFY LADRKIRSGR  60
HSLDVLIENG DWVAARGVFT GQLRTGEAVT TRWADFHQFR GEKIWRRYTY FADQSV      116

SEQ ID NO: 5            moltype = DNA  length = 1242
FEATURE                 Location/Qualifiers
source                  1..1242
                        mol_type = other DNA
                        note = Codon-optimized dsaD including 6x His-tag
                        organism = synthetic construct
SEQUENCE: 5
atgggcagca gccatcatca tcatcatcac agcagcggcc tggtgccgcg cggcagccat  60
atggctagca tgactggtgg acagcaaatg ggtcgcggat ccgaattcat gcatattgtc  120
acgacccctg ttgcgcgtcc gctgacagcg caggagcgga cagagcggtg tgctgccccg  180
gcgtttggaa cggcgtttac cgagcacatg gtaagtgcca gatggaatcc cgagcaaggg  240
tggcatgatg cggaattagt gccctatggt ccgttgttgc tggacccagc gacagtcggc  300
ttgcactatg ggcaagtagt tttcgaaggg ttgaaagcat ttcggagtca taccggagaa  360
gtagccgtgt tccggccgga cgcccacgcc gaacggatgc gcgcatccgc tcgcagactt  420
atgatgcctg aacctccaga ggaattattt cttgccgcgg tggatgcgct ggtggcacaa  480
gatcaagagt ggatccctga tgaccctggt atgtccttat atctgcgccc gattcttttc  540
gcctcagagc ggacgttggc tcttcgtcca gcgcgcgaat atcgctttct tttagtagca  600
tttataaccg aaggatactt tggacctgct caaagacccg ttcgtgtctg ggtgacagat  660
gaatacagta gagccgcagc gggtggaacg ggagcggcca agtgcgcggg caactatgct  720
gggagcttac tggcacaaga ggaggcacaa cgcaaaggtt gtgaccaagt ggtgtggtta  780
gatccggttg agcgtaactg ggtggaggag atgggcggca tgaacttatt ttttgtctac  840
gaggcggggg ggtcagcccg gctggtaacg ccgccgctta ctggatccct gcttcccggt  900
gttacccgcg acgccttgtt gcggcttgcc cctacgcttg gtgtcccagt gtctgaagct  960
ccgctttcac ttgaacagtg gcgggcggac tgtgcgagtg gcgctatcac cgaagtcttt  1020
gcctgcggca ctgcggcccg catctcgccc gtgaacgaag ttagcactaa ggacggttcg  1080
tggaccattg ggcaggagc cccggcagaa ggaggggtcg ctgccggtga agtaaccggt  1140
agattatcgg cggccttatt tggaatccag agaggcgaac ttcctgattc gcatagttgg  1200
atgcgccctg tctcacctgc acggcaatcg gccataactt aa                     1242

SEQ ID NO: 6            moltype = AA  length = 413
FEATURE                 Location/Qualifiers
source                  1..413
                        mol_type = protein
                        note = DsaD including 6x His-tag
                        organism = synthetic construct
SEQUENCE: 6
MGSSHHHHHH SSGLVPRGSH MASMTGGQQM GRGSEFMHIV TTPVARPLTA QERTERCAAP  60
AFGTAFTEHM VSARWNPEQG WHDAELVPYG PLLLDPATVG LHYGQVVFEG LKAFRSHTGE  120
VAVFRPDAHA ERMRASARRL MMPEPPEELF LAAVDALVAQ DQEWIPDDPG MSLYLRPILF  180
```

-continued

```
ASERTLALRP AREYRFLLVA FITEGYFGPA QRPVRVWVTD EYSRAAAGGT GAAKCAGNYA  240
GSLLAQEEAQ RKGCDQVVWL DPVERNWVEE MGGMNLFFVY EAGGSARLVT PPLTGSLLPG  300
VTRDALLRLA PTLGVPVSEA PLSLEQWRAD CASGAITEVF ACGTAARISP VNEVSTKDGS  360
WTIGAGAPAE GGVAAGEVTG RLSAALFGIQ RGELPDSHSW MRPVSPARQS AIT         413

SEQ ID NO: 7           moltype = DNA  length = 483
FEATURE                Location/Qualifiers
source                 1..483
                       mol_type = other DNA
                       note = Codon-optimized dsaE including 6s His-tag
                       organism = synthetic construct
SEQUENCE: 7
atgggcagca gccatcatca tcatcatcac agcagcggcc tggtgccgcg cggcagccat  60
atggctagca tgactggtgg acagcaaatg ggtcgcggat ccgaattcat gacagagtcg  120
agtccgactg aagtgaatga ggctcgtgtt agagaatact atcggttggt tgacgcggac  180
gacgttttgg gtttagtgtc cttatttgca gaggacgccg tttatcgtcg gcccggttat  240
gagccaatga gagggcacac tggcttaact gcgttttaca caggcgaacg tgtcattgag  300
tccggccgcc acaccgttgc tacagtggtc gcacgcggag accaagtagc tgttaatgga  360
gtctttgaag ggtccttaa ggatgggaga caagttcggc tggaatttgc cgatttcttc  420
ttgttaaatg gggaacgcag atttcccgg cgggacactt attttttgc ccctctggtg  480
taa                                                               483

SEQ ID NO: 8           moltype = AA  length = 160
FEATURE                Location/Qualifiers
source                 1..160
                       mol_type = protein
                       note = DsaE including 6x His-tag
                       organism = synthetic construct
SEQUENCE: 8
MGSSHHHHHH SSGLVPRGSH MASMTGGQQM GRGSEFMTES SPTEVNEARV REYYRLVDAD  60
DVLGLVSLFA EDAVYRRPGY EPMRGHTGLT AFYTGERVIE SGRHTVATVV ARGDQVAVNG  120
VFEGVLKDGR QVRLEFADFF LLNGERRFSR RDTYFFAPLV                        160

SEQ ID NO: 9           moltype = DNA  length = 459
FEATURE                Location/Qualifiers
source                 1..459
                       mol_type = other DNA
                       note = Condon-optimized mfnH including 6x His-tag
                       organism = synthetic construct
SEQUENCE: 9
atgggcagca gccatcatca tcatcatcac agcagcggcc tggtgccgcg cggcagccat  60
atggctagca tgactggtgg acagcaaatg ggtcgcggat ccgaattcat gggccgttct  120
gagaccattc gccggtacta cgagcttgtg gacgccgctg actatgaagc catgtttaga  180
atcttctgcg atgaccttat atacgagcgg gcaggcactg aaccaataga agggatagtt  240
gagttccgtc atttttattt ggctgaccgc aaaattcgct ctgggcggca ttcgcttgac  300
gtcttgatag aaaatggcga ctgggtagca gcacggggag tttttactgg gcaactgcgc  360
actggtgaag cggtgacgac ccggtgggct gactttcatc aatttagagg ggagaagatt  420
tggcgcagat acacatactt cgccgaccag tcggtctaa                         459

SEQ ID NO: 10          moltype = AA  length = 152
FEATURE                Location/Qualifiers
source                 1..152
                       mol_type = protein
                       note = MfnH including 6x His-tag
                       organism = synthetic construct
SEQUENCE: 10
MGSSHHHHHH SSGLVPRGSH MASMTGGQQM GRGSEFMGRS ETIRRYYELV DAADYEAMFR  60
IFCDDLIYER AGTEPIEGIV EFRHFYLADR KIRSGRHSLD VLIENGDWVA ARGVFTGQLR  120
TGEAVTTRWA DFHQFRGEKI WRRYTYFADQ SV                                152
```